US010041055B2

(12) United States Patent
Krogh et al.

(10) Patent No.: US 10,041,055 B2
(45) Date of Patent: Aug. 7, 2018

(54) POLYPEPTIDES HAVING MANNANASE ACTIVITY AND POLYNUCLEOTIDES ENCODING SAME

(71) Applicant: Novozymes A/S, Bagsvaerd (DK)

(72) Inventors: Kristian Bertel Roemer M. Krogh, Bagsvaerd (DK); Nikolaj Spodsberg, Bagsvaerd (DK); Klaus Gori, Copenhagen (DK); Pernille Von Freiesleben, Bagsvaerd (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 14/916,476

(22) PCT Filed: Sep. 19, 2014

(86) PCT No.: PCT/EP2014/069992
§ 371 (c)(1),
(2) Date: Mar. 3, 2016

(87) PCT Pub. No.: WO2015/040159
PCT Pub. Date: Mar. 26, 2015

(65) Prior Publication Data
US 2017/0183643 A1  Jun. 29, 2017

(30) Foreign Application Priority Data

Sep. 19, 2013 (EP) .................................. 13185155
Jun. 20, 2014 (EP) .................................. 14173278

(51) Int. Cl.
| | |
|---|---|
| *C12N 9/42* | (2006.01) |
| *C12N 9/24* | (2006.01) |
| *C12N 9/14* | (2006.01) |
| *C12P 19/14* | (2006.01) |
| *C12P 21/06* | (2006.01) |
| *C12P 19/34* | (2006.01) |
| *C12N 15/00* | (2006.01) |
| *C12N 1/20* | (2006.01) |
| *C12N 1/00* | (2006.01) |
| *C12N 9/16* | (2006.01) |
| *C12N 9/02* | (2006.01) |
| *C12N 9/88* | (2006.01) |
| *C12N 9/48* | (2006.01) |
| *C12P 19/02* | (2006.01) |
| *C09K 8/62* | (2006.01) |
| *C09K 8/52* | (2006.01) |
| *C11D 3/386* | (2006.01) |
| *A23F 5/24* | (2006.01) |

(52) U.S. Cl.
CPC ............ *C12N 9/2494* (2013.01); *A23F 5/246* (2013.01); *C09K 8/52* (2013.01); *C09K 8/62* (2013.01); *C11D 3/38636* (2013.01); *C12N 9/0004* (2013.01); *C12N 9/16* (2013.01); *C12N 9/2402* (2013.01); *C12N 9/2437* (2013.01); *C12N 9/48* (2013.01); *C12N 9/88* (2013.01); *C12P 19/02* (2013.01); *C12P 19/14* (2013.01); *C12Y 302/01004* (2013.01); *C12Y 302/01078* (2013.01); *C12Y 402/0201* (2013.01)

(58) Field of Classification Search
CPC .. C12N 9/2494; C12N 9/2437; C12N 9/2402; C12N 9/16; C12N 9/0004; C12N 9/88; C12N 9/48; C12Y 302/01078; C12Y 402/0201; C12Y 302/1004; C12P 19/02; C12P 19/14; C09K 8/62; C09K 8/52; C11D 3/38636; A23F 5/246
USPC .... 435/209, 200, 195, 99, 69.1, 91.1, 320.1, 435/252.3, 254.11; 536/23.1, 23.2; 530/350
See application file for complete search history.

(56) References Cited

FOREIGN PATENT DOCUMENTS

WO        9964619 A2    12/1999

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Saponins, 2 pages, http://www.ecologicalsurfactants.com/saponin/, retrieved, Mar. 13, 2014 (Year: 2014).*
Surfactants, 8 pages, http://www.rsc.org/chemistryworld/issues/2003/july/amphiphiles.asp/, retrieved Mar. 13, 2014 (Year: 2014).*
Cai et al, 2011, J Biosci Bioeng, vol. 112, No. 6, pp. 551-557.
Couturier et al, 2013, J. Biol. Chem, vol. 288, No. 20, pp. 14624-14635.
Fungal Genetics and Biology, vol. 46 (2009), pp. S2Â-S13.
Jorgensen et al, 2010, Appl Biochem Biotech, vol. 161, pp. 318-332.
Nunes et al, 2006, J. Agric Food Chem, vol. 54, No. 9, pp. 3428Â-3439.
Staelbrand et al, 1995, App Envi Micro, vol. 61, pp. 1090-1097.
Varnai et al, 2011, Bioresource Tech, vol. 102, pp. 9096-9104.

* cited by examiner

*Primary Examiner* — Ganapathirama Raghu
(74) *Attorney, Agent, or Firm* — Todd Sladek

(57) ABSTRACT

The present invention relates to polypeptides having mannanase activity, catalytic domains, and carbohydrate binding modules, and polynucleotides encoding the polypeptides, catalytic domains, and carbohydrate binding modules. The invention also relates to nucleic acid constructs, vectors, and host cells comprising the polynucleotides as well as methods of producing and using the polypeptides, catalytic domains, and carbohydrate binding modules.

16 Claims, 1 Drawing Sheet

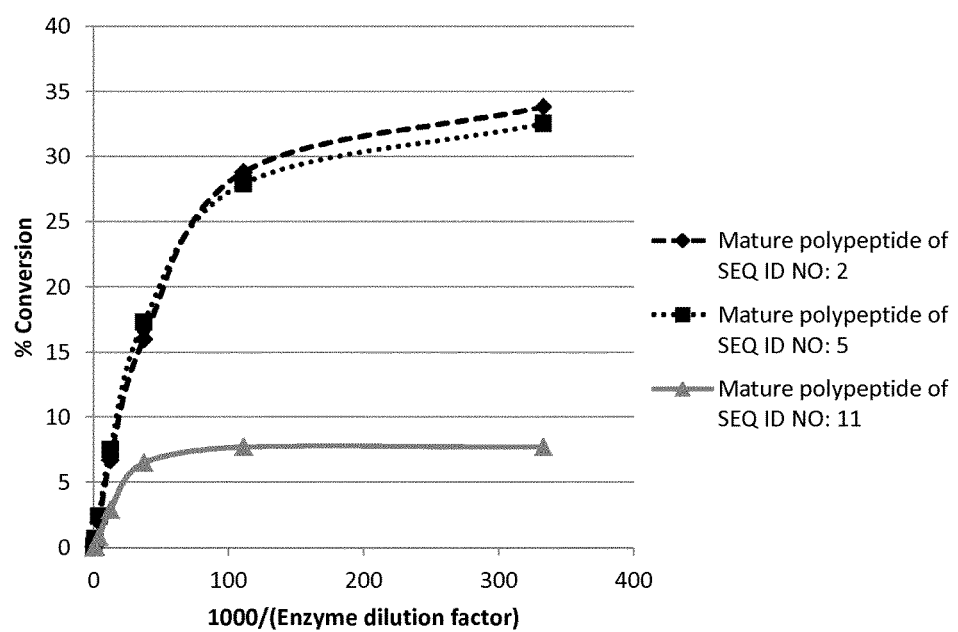

SEQUENCE LISTING

```
<160> NUMBER OF SEQ ID NOS: 11

<210> SEQ ID NO 1
<211> LENGTH: 1734
<212> TYPE: DNA
<213> ORGANISM: Ascobolus stictoideus
<220> FEATURE:
<221> NAME/KEY: sig_peptide
<222> LOCATION: (1)..(60)
<220> FEATURE:
<221> NAME/KEY: sig_peptide
<222> LOCATION: (1)..(60)
<220> FEATURE:
<221> NAME/KEY: CDS
<222> LOCATION: (1)..(395)
<220> FEATURE:
<221> NAME/KEY: mat_peptide
<222> LOCATION: (61)..(1731)
<220> FEATURE:
<221> NAME/KEY: CDS
<222> LOCATION: (444)..(1731)

<400> SEQUENCE: 1 atg cgt ttc tct ctc tgc gtc gga tcc gct ctt gtg gct ttc gcc aca        48
Met Arg Phe Ser Leu Cys Val Gly Ser Ala Leu Val Ala Phe Ala Thr
-20              -15                  -10                  -5 tct gcc ttt gct cag act tac acc ctt gag gcc gag gct gga act ctg        96
Ser Ala Phe Ala Gln Thr Tyr Thr Leu Glu Ala Glu Ala Gly Thr Leu
         -1   1               5                  10 act gga gta act gtc atg aac gag att gct ggt ttc tct gga act ggt       144
Thr Gly Val Thr Val Met Asn Glu Ile Ala Gly Phe Ser Gly Thr Gly
             15                  20                  25 tat gtt ggt gga tgg gac gag gat gct gat acc gtt tcc ctc acc ttc       192
Tyr Val Gly Gly Trp Asp Glu Asp Ala Asp Thr Val Ser Leu Thr Phe
         30                  35                  40 acc tcg gac gcc acc aag ctc tac gac gtc aag atc cgt tac tct gga       240
Thr Ser Asp Ala Thr Lys Leu Tyr Asp Val Lys Ile Arg Tyr Ser Gly
45                  50                  55                  60 cca tat ggc tcc aag tat acc cgc atc agc tac aac ggt gcc act gga       288
Pro Tyr Gly Ser Lys Tyr Thr Arg Ile Ser Tyr Asn Gly Ala Thr Gly
             65                  70                  75
```

```
gga gac atc tct ctt cca gag acc act gag tgg gca act gtc aat gct        336
Gly Asp Ile Ser Leu Pro Glu Thr Thr Glu Trp Ala Thr Val Asn Ala
            80                  85                  90 gga cag gct ctc ttg aac gcc ggt tcc aac acc atc aag ctt cac aac        384
Gly Gln Ala Leu Leu Asn Ala Gly Ser Asn Thr Ile Lys Leu His Asn
        95                 100                 105 aac tgg gga tg  gtaagttctg tcactgattc aataagataa atgctaacag            435
Asn Trp Gly Trp
    110 tctgccag g tac ttg att gat gcc gtc att ctt act ccc tcc gtt cca         483
           Tyr Leu Ile Asp Ala Val Ile Leu Thr Pro Ser Val Pro
               115                 120                 125 cgc cct ccc cat caa gtc act gat gcc ctt gtc aac acc aac tcc aac        531
Arg Pro Pro His Gln Val Thr Asp Ala Leu Val Asn Thr Asn Ser Asn
                130                 135                 140 gct gtc acc aag cag ctc atg aag ttc ctc gtt tcc aag tat cac aag        579
Ala Val Thr Lys Gln Leu Met Lys Phe Leu Val Ser Lys Tyr His Lys
            145                 150                 155 gct tat att acc ggt caa caa gag ctt cat gcc cac cag tgg gtt gag        627
Ala Tyr Ile Thr Gly Gln Gln Glu Leu His Ala His Gln Trp Val Glu
        160                 165                 170 aag aac gtt ggg aag tcc cca gct att ctc ggt ctc gat ttc atg gat        675
Lys Asn Val Gly Lys Ser Pro Ala Ile Leu Gly Leu Asp Phe Met Asp
    175                 180                 185 tac tct cca tcc aga gtt gag ttc ggc act acc tca cag gct gtt gag        723
Tyr Ser Pro Ser Arg Val Glu Phe Gly Thr Thr Ser Gln Ala Val Glu
190                 195                 200                 205 cag gcc att gat ttc gac aag aga ggg ggt att gtt acc ttt gct tgg        771
Gln Ala Ile Asp Phe Asp Lys Arg Gly Gly Ile Val Thr Phe Ala Trp
                210                 215                 220 cac tgg aac gct cca tcc ggt ctc atc aac act ccc ggt tct gaa tgg        819
His Trp Asn Ala Pro Ser Gly Leu Ile Asn Thr Pro Gly Ser Glu Trp
            225                 230                 235 tgg cgc gga ttc tat act gag cac acc acc ttc gat gtt gct gct gct        867
Trp Arg Gly Phe Tyr Thr Glu His Thr Thr Phe Asp Val Ala Ala Ala
        240                 245                 250 ctc caa aac acc acc aac gcc aac tac aac ctt ctc att cgc gac att        915
Leu Gln Asn Thr Thr Asn Ala Asn Tyr Asn Leu Leu Ile Arg Asp Ile
    255                 260                 265 gac gcc atc gct gtc caa ttg aag aga ctt caa act gct ggc gtc cca        963
Asp Ala Ile Ala Val Gln Leu Lys Arg Leu Gln Thr Ala Gly Val Pro
270                 275                 280                 285 gtt ctc tgg cgt cca ctt cac gag gcc gag gga gga tgg ttc tgg tgg       1011
Val Leu Trp Arg Pro Leu His Glu Ala Glu Gly Gly Trp Phe Trp Trp
                290                 295                 300 gga gcc aag ggt ccc gag cca gcc aag aag ctc tac aag atc ctc tac       1059
Gly Ala Lys Gly Pro Glu Pro Ala Lys Lys Leu Tyr Lys Ile Leu Tyr
            305                 310                 315 gac cgt ctc acc aac tac cac aag ctc aac aac ctc atc tgg gtg tgg       1107
Asp Arg Leu Thr Asn Tyr His Lys Leu Asn Asn Leu Ile Trp Val Trp
        320                 325                 330 aac tct gtc gca aag gac tgg tac cct ggt gat gag atc gtc gat gtt       1155
Asn Ser Val Ala Lys Asp Trp Tyr Pro Gly Asp Glu Ile Val Asp Val
    335                 340                 345 ctc tcc ttc gat tct tac cca gct caa cct gga gat cac gga cca gtt       1203
Leu Ser Phe Asp Ser Tyr Pro Ala Gln Pro Gly Asp His Gly Pro Val
350                 355                 360                 365 tct gct caa tac aac gcc ctc gtc gag ctc ggc aag gac aag aag ttg       1251
Ser Ala Gln Tyr Asn Ala Leu Val Glu Leu Gly Lys Asp Lys Lys Leu
                370                 375                 380
```

-continued

| | |
|---|---|
| att gct gcc act gaa gtc ggt acc atc cca gac cca gat ctc atg cag<br>Ile Ala Ala Thr Glu Val Gly Thr Ile Pro Asp Pro Asp Leu Met Gln<br>            385                      390                  395 | 1299 |
| ctc tac gaa tct tac tgg tct ttc ttc gtc aca tgg gag gga gag ttc<br>Leu Tyr Glu Ser Tyr Trp Ser Phe Phe Val Thr Trp Glu Gly Glu Phe<br>        400                      405                  410 | 1347 |
| att gag aac ggc gtc cat aac tcc ctt gag ttc ctc aag aag ctc tac<br>Ile Glu Asn Gly Val His Asn Ser Leu Glu Phe Leu Lys Lys Leu Tyr<br>415                      420                      425 | 1395 |
| aac aac tcg ttc gtc ctc aac ctt gac acc atc cag ggc tgg aag aac<br>Asn Asn Ser Phe Val Leu Asn Leu Asp Thr Ile Gln Gly Trp Lys Asn<br>430                      435                      440                  445 | 1443 |
| ggt gct ggt tca tcc acc acc acc gtc aag tcc acc acc acc cca<br>Gly Ala Gly Ser Ser Thr Thr Thr Val Lys Ser Thr Thr Thr Pro<br>              450                      455                      460 | 1491 |
| acc acc acc atc aag tct acc acc acc acc cca gtc acc acc cca act<br>Thr Thr Thr Ile Lys Ser Thr Thr Thr Thr Pro Val Thr Thr Pro Thr<br>            465                      470                      475 | 1539 |
| acc gtc aag acc acc acc acc cca act acc acc gca acc acc gtt aag<br>Thr Val Lys Thr Thr Thr Thr Pro Thr Thr Thr Ala Thr Thr Val Lys<br>480                      485                      490 | 1587 |
| tcc acc acc acc gct ggc cca acc cca act gct gtc gct ggc aga<br>Ser Thr Thr Thr Ala Gly Pro Thr Pro Thr Ala Val Ala Gly Arg<br>495                      500                      505 | 1635 |
| tgg caa cag tgc ggt gga atc ggc ttc acc ggc cca acc act tgc gag<br>Trp Gln Gln Cys Gly Gly Ile Gly Phe Thr Gly Pro Thr Thr Cys Glu<br>510                      515                      520                  525 | 1683 |
| gct gga acc acc tgc aat gtc ctc aac cca tac tac tct cag tgc ttg<br>Ala Gly Thr Thr Cys Asn Val Leu Asn Pro Tyr Tyr Ser Gln Cys Leu<br>                  530                      535                  540 | 1731 |
| taa | 1734 |

<210> SEQ ID NO 2
<211> LENGTH: 561
<212> TYPE: PRT
<213> ORGANISM: Ascobolus stictoideus

<400> SEQUENCE: 2

Met Arg Phe Ser Leu Cys Val Gly Ser Ala Leu Val Ala Phe Ala Thr
-20              -15                 -10                  -5

Ser Ala Phe Ala Gln Thr Tyr Thr Leu Glu Ala Glu Ala Gly Thr Leu
             -1  1               5                   10

Thr Gly Val Thr Val Met Asn Glu Ile Ala Gly Phe Ser Gly Thr Gly
        15                  20                  25

Tyr Val Gly Gly Trp Asp Glu Asp Ala Asp Thr Val Ser Leu Thr Phe
    30                  35                  40

Thr Ser Asp Ala Thr Lys Leu Tyr Asp Val Lys Ile Arg Tyr Ser Gly
45                  50                  55                  60

Pro Tyr Gly Ser Lys Tyr Thr Arg Ile Ser Tyr Asn Gly Ala Thr Gly
                65                  70                  75

Gly Asp Ile Ser Leu Pro Glu Thr Thr Glu Trp Ala Thr Val Asn Ala
            80                  85                  90

Gly Gln Ala Leu Leu Asn Ala Gly Ser Asn Thr Ile Lys Leu His Asn
        95                  100                 105

Asn Trp Gly Trp Tyr Leu Ile Asp Ala Val Ile Leu Thr Pro Ser Val
    110                 115                 120

Pro Arg Pro Pro His Gln Val Thr Asp Ala Leu Val Asn Thr Asn Ser
125                 130                 135                 140

```
Asn Ala Val Thr Lys Gln Leu Met Lys Phe Leu Val Ser Lys Tyr His
                145                 150                 155
Lys Ala Tyr Ile Thr Gly Gln Gln Glu Leu His Ala His Gln Trp Val
            160                 165                 170
Glu Lys Asn Val Gly Lys Ser Pro Ala Ile Leu Gly Leu Asp Phe Met
        175                 180                 185
Asp Tyr Ser Pro Ser Arg Val Glu Phe Gly Thr Thr Ser Gln Ala Val
    190                 195                 200
Glu Gln Ala Ile Asp Phe Asp Lys Arg Gly Gly Ile Val Thr Phe Ala
205                 210                 215                 220
Trp His Trp Asn Ala Pro Ser Gly Leu Ile Asn Thr Pro Gly Ser Glu
                225                 230                 235
Trp Trp Arg Gly Phe Tyr Thr Glu His Thr Thr Phe Asp Val Ala Ala
            240                 245                 250
Ala Leu Gln Asn Thr Thr Asn Ala Asn Tyr Asn Leu Leu Ile Arg Asp
        255                 260                 265
Ile Asp Ala Ile Ala Val Gln Leu Lys Arg Leu Gln Thr Ala Gly Val
    270                 275                 280
Pro Val Leu Trp Arg Pro Leu His Glu Ala Glu Gly Gly Trp Phe Trp
285                 290                 295                 300
Trp Gly Ala Lys Gly Pro Glu Pro Ala Lys Lys Leu Tyr Lys Ile Leu
                305                 310                 315
Tyr Asp Arg Leu Thr Asn Tyr His Lys Leu Asn Asn Leu Ile Trp Val
            320                 325                 330
Trp Asn Ser Val Ala Lys Asp Trp Tyr Pro Gly Asp Glu Ile Val Asp
        335                 340                 345
Val Leu Ser Phe Asp Ser Tyr Pro Ala Gln Pro Gly Asp His Gly Pro
    350                 355                 360
Val Ser Ala Gln Tyr Asn Ala Leu Val Glu Leu Gly Lys Asp Lys Lys
365                 370                 375                 380
Leu Ile Ala Ala Thr Glu Val Gly Thr Ile Pro Asp Pro Asp Leu Met
                385                 390                 395
Gln Leu Tyr Glu Ser Tyr Trp Ser Phe Val Thr Trp Glu Gly Glu
            400                 405                 410
Phe Ile Glu Asn Gly Val His Asn Ser Leu Glu Phe Leu Lys Lys Leu
        415                 420                 425
Tyr Asn Asn Ser Phe Val Leu Asn Leu Asp Thr Ile Gln Gly Trp Lys
    430                 435                 440
Asn Gly Ala Gly Ser Ser Thr Thr Thr Val Lys Ser Thr Thr Thr Thr
445                 450                 455                 460
Pro Thr Thr Thr Ile Lys Ser Thr Thr Thr Pro Val Thr Thr Pro
                465                 470                 475
Thr Thr Val Lys Thr Thr Thr Thr Pro Thr Thr Thr Ala Thr Thr Val
            480                 485                 490
Lys Ser Thr Thr Thr Thr Ala Gly Pro Thr Pro Thr Ala Val Ala Gly
        495                 500                 505
Arg Trp Gln Gln Cys Gly Gly Ile Gly Phe Thr Gly Pro Thr Thr Cys
    510                 515                 520
Glu Ala Gly Thr Thr Cys Asn Val Leu Asn Pro Tyr Tyr Ser Gln Cys
525                 530                 535                 540
Leu
```

<210> SEQ ID NO 3
<211> LENGTH: 541
<212> TYPE: PRT
<213> ORGANISM: Ascobolus stictoideus

<400> SEQUENCE: 3

```
Gln Thr Tyr Thr Leu Glu Ala Glu Ala Gly Thr Leu Thr Gly Val Thr
1               5                   10                  15

Val Met Asn Glu Ile Ala Gly Phe Ser Gly Thr Gly Tyr Val Gly Gly
            20                  25                  30

Trp Asp Glu Asp Ala Asp Thr Val Ser Leu Thr Phe Thr Ser Asp Ala
        35                  40                  45

Thr Lys Leu Tyr Asp Val Lys Ile Arg Tyr Ser Gly Pro Tyr Gly Ser
50                  55                  60

Lys Tyr Thr Arg Ile Ser Tyr Asn Gly Ala Thr Gly Gly Asp Ile Ser
65                  70                  75                  80

Leu Pro Glu Thr Thr Glu Trp Ala Thr Val Asn Ala Gly Gln Ala Leu
                85                  90                  95

Leu Asn Ala Gly Ser Asn Thr Ile Lys Leu His Asn Asn Trp Gly Trp
            100                 105                 110

Tyr Leu Ile Asp Ala Val Ile Leu Thr Pro Ser Val Pro Arg Pro Pro
        115                 120                 125

His Gln Val Thr Asp Ala Leu Val Asn Thr Asn Ser Asn Ala Val Thr
130                 135                 140

Lys Gln Leu Met Lys Phe Leu Val Ser Lys Tyr His Lys Ala Tyr Ile
145                 150                 155                 160

Thr Gly Gln Gln Glu Leu His Ala His Gln Trp Val Glu Lys Asn Val
                165                 170                 175

Gly Lys Ser Pro Ala Ile Leu Gly Leu Asp Phe Met Asp Tyr Ser Pro
            180                 185                 190

Ser Arg Val Glu Phe Gly Thr Thr Ser Gln Ala Val Glu Gln Ala Ile
        195                 200                 205

Asp Phe Asp Lys Arg Gly Gly Ile Val Thr Phe Ala Trp His Trp Asn
210                 215                 220

Ala Pro Ser Gly Leu Ile Asn Thr Pro Gly Ser Glu Trp Trp Arg Gly
225                 230                 235                 240

Phe Tyr Thr Glu His Thr Thr Phe Asp Val Ala Ala Leu Gln Asn
                245                 250                 255

Thr Thr Asn Ala Asn Tyr Asn Leu Leu Ile Arg Asp Ile Asp Ala Ile
            260                 265                 270

Ala Val Gln Leu Lys Arg Leu Gln Thr Ala Gly Val Pro Val Leu Trp
        275                 280                 285

Arg Pro Leu His Glu Ala Glu Gly Gly Trp Phe Trp Trp Gly Ala Lys
290                 295                 300

Gly Pro Glu Pro Ala Lys Lys Leu Tyr Lys Ile Leu Tyr Asp Arg Leu
305                 310                 315                 320

Thr Asn Tyr His Lys Leu Asn Asn Leu Ile Trp Val Trp Asn Ser Val
                325                 330                 335

Ala Lys Asp Trp Tyr Pro Gly Asp Glu Ile Val Asp Val Leu Ser Phe
            340                 345                 350

Asp Ser Tyr Pro Ala Gln Pro Gly Asp His Gly Pro Val Ser Ala Gln
        355                 360                 365

Tyr Asn Ala Leu Val Glu Leu Gly Lys Asp Lys Lys Leu Ile Ala Ala
370                 375                 380
```

```
Thr Glu Val Gly Thr Ile Pro Asp Pro Asp Leu Met Gln Leu Tyr Glu
385                 390                 395                 400

Ser Tyr Trp Ser Phe Phe Val Thr Trp Glu Gly Glu Phe Ile Glu Asn
            405                 410                 415

Gly Val His Asn Ser Leu Glu Phe Leu Lys Lys Leu Tyr Asn Asn Ser
        420                 425                 430

Phe Val Leu Asn Leu Asp Thr Ile Gln Gly Trp Lys Asn Gly Ala Gly
        435                 440                 445

Ser Ser Thr Thr Thr Val Lys Ser Thr Thr Thr Pro Thr Thr Thr
    450                 455                 460

Ile Lys Ser Thr Thr Thr Thr Pro Val Thr Thr Pro Thr Thr Val Lys
465                 470                 475                 480

Thr Thr Thr Thr Pro Thr Thr Thr Ala Thr Thr Val Lys Ser Thr Thr
                485                 490                 495

Thr Thr Ala Gly Pro Thr Pro Thr Ala Val Ala Gly Arg Trp Gln Gln
            500                 505                 510

Cys Gly Gly Ile Gly Phe Thr Gly Pro Thr Thr Cys Glu Ala Gly Thr
            515                 520                 525

Thr Cys Asn Val Leu Asn Pro Tyr Tyr Ser Gln Cys Leu
    530                 535                 540

<210> SEQ ID NO 4
<211> LENGTH: 1888
<212> TYPE: DNA
<213> ORGANISM: Chaetomium virescens
<220> FEATURE:
<221> NAME/KEY: CDS
<222> LOCATION: (1)..(172)
<220> FEATURE:
<221> NAME/KEY: sig_peptide
<222> LOCATION: (1)..(63)
<220> FEATURE:
<221> NAME/KEY: mat_peptide
<222> LOCATION: (79)..(1885)
<220> FEATURE:
<221> NAME/KEY: CDS
<222> LOCATION: (238)..(496)
<220> FEATURE:
<221> NAME/KEY: CDS
<222> LOCATION: (550)..(1294)
<220> FEATURE:
<221> NAME/KEY: CDS
<222> LOCATION: (1351)..(1542)
<220> FEATURE:
<221> NAME/KEY: CDS
<222> LOCATION: (1598)..(1885)

<400> SEQUENCE: 4 atg gac aaa atc ctc aga tac ttt ctc tgc ggc atc ata gcc ttg gct      48
Met Asp Lys Ile Leu Arg Tyr Phe Leu Cys Gly Ile Ile Ala Leu Ala
    -25                 -20                 -15 ggg gcc aca act gcg gcg cca tcg tat cag ccg cgg gat ccc ggc gca      96
Gly Ala Thr Thr Ala Ala Pro Ser Tyr Gln Pro Arg Asp Pro Gly Ala
-10                 -5                 -1   1                 5 act gct cgg acg ttt gag gct gag gat gca aca ctg gcc ggg acg aat     144
Thr Ala Arg Thr Phe Glu Ala Glu Asp Ala Thr Leu Ala Gly Thr Asn
                10                  15                  20 gtc gac acg gcg ctg tct ggg ttt acc g gtaggcatcc cagctccta           192
Val Asp Thr Ala Leu Ser Gly Phe Thr
                25                  30 tatccgggag tcaacccatt gcgctaatcg tggacatgaa cacag gc  act ggc tac    248
                                                 Gly Thr Gly Tyr
                                                         35
```

| | | |
|---|---|---|
| gtc acc ggc ttc gac cag gca gct gac aag gtc acg ttt act gtt gac<br>Val Thr Gly Phe Asp Gln Ala Ala Asp Lys Val Thr Phe Thr Val Asp<br>40                         45                    50 | 296 |
| agt gcc agc act gaa ctg tat gac ctc agc atc cgt gtt gcc gcc atc<br>Ser Ala Ser Thr Glu Leu Tyr Asp Leu Ser Ile Arg Val Ala Ala Ile<br>             55                    60                    65 | 344 |
| tac ggc gac aag cgt acc tcg gta gtc ctc aat gga ggg gct agc agt<br>Tyr Gly Asp Lys Arg Thr Ser Val Val Leu Asn Gly Gly Ala Ser Ser<br>     70                    75                  80 | 392 |
| gag gta tat ttc cca gcc ggc gaa acg tgg acc aat gtc gct gcc ggc<br>Glu Val Tyr Phe Pro Ala Gly Glu Thr Trp Thr Asn Val Ala Ala Gly<br>85                         90                    95 | 440 |
| cag ctc ctc ctc aac cag ggc tcc aac acg ata gac atc gtc agc aac<br>Gln Leu Leu Leu Asn Gln Gly Ser Asn Thr Ile Asp Ile Val Ser Asn<br>100                   105                110                115 | 488 |
| tgg gga tg   gtaagtcacg gcatacattt cagccgacag acacagctaa<br>Trp Gly Trp | 536 |
| caattccgtc cag g tac ctc atc gac tcc atc aca ctc act ccc tcg acc<br>                    Tyr Leu Ile Asp Ser Ile Thr Leu Thr Pro Ser Thr<br>                       120                125                130 | 586 |
| ccc cgc ccg gca cac caa atc aat gaa gcg cca gtc aac gcg gcc gcg<br>Pro Arg Pro Ala His Gln Ile Asn Glu Ala Pro Val Asn Ala Ala Ala<br>               135                140                145 | 634 |
| gac aag aac gca aag gcc tta tac agc tac ctc cgt tcc atc tac ggc<br>Asp Lys Asn Ala Lys Ala Leu Tyr Ser Tyr Leu Arg Ser Ile Tyr Gly<br>          150                155                160 | 682 |
| aag aag atc ctc tcg ggc cag cag gaa ctc tcg ttg tcc aac tgg atc<br>Lys Lys Ile Leu Ser Gly Gln Gln Glu Leu Ser Leu Ser Asn Trp Ile<br>             165                170                175 | 730 |
| gcc cag cag acg ggc aag acg ccg gca ctt gtc tcg gta gat ctc atg<br>Ala Gln Gln Thr Gly Lys Thr Pro Ala Leu Val Ser Val Asp Leu Met<br>180                       185                   190 | 778 |
| gac tac tcg ccc tcg cgc gtc gaa agg ggc acg gtt ggg act gca gtc<br>Asp Tyr Ser Pro Ser Arg Val Glu Arg Gly Thr Val Gly Thr Ala Val<br>195                    200                205                210 | 826 |
| gag gag gcc atc cag cac cac aac cgc ggc ggc atc gtc tca gtt ctc<br>Glu Glu Ala Ile Gln His His Asn Arg Gly Gly Ile Val Ser Val Leu<br>               215                220                225 | 874 |
| tgg cac tgg aac gcg ccg aca ggt ctc tac gac acc gag gag cat cgg<br>Trp His Trp Asn Ala Pro Thr Gly Leu Tyr Asp Thr Glu Glu His Arg<br>          230                235                240 | 922 |
| tgg tgg agt ggc ttc tac acg tcc gcg act gat ttt gat gtt gca gcg<br>Trp Trp Ser Gly Phe Tyr Thr Ser Ala Thr Asp Phe Asp Val Ala Ala<br>             245                250                255 | 970 |
| gcg ctc agc tcg acc acg aat gcc aac tac acg ctt ctc atc agg gac<br>Ala Leu Ser Ser Thr Thr Asn Ala Asn Tyr Thr Leu Leu Ile Arg Asp<br>260                       265                270 | 1018 |
| atc gac gcc atc gca gtc cag ctc aag cgg ttg cag tcg gcc ggc gtg<br>Ile Asp Ala Ile Ala Val Gln Leu Lys Arg Leu Gln Ser Ala Gly Val<br>275                       280                285                290 | 1066 |
| ccc gtc ttg ttc cgg ccg ctg cat gag gcc gaa ggt ggt tgg ttc tgg<br>Pro Val Leu Phe Arg Pro Leu His Glu Ala Glu Gly Gly Trp Phe Trp<br>               295                300                305 | 1114 |
| tgg ggt gca aag ggg ccc gag ccg gcc aag aaa ctc tgg ggt atc ctg<br>Trp Gly Ala Lys Gly Pro Glu Pro Ala Lys Lys Leu Trp Gly Ile Leu<br>          310                315                320 | 1162 |
| tat gat cgg gtt acc aac cac cac cag att aac aac ctc ctt tgg gtc<br>Tyr Asp Arg Val Thr Asn His His Gln Ile Asn Asn Leu Leu Trp Val<br>325                       330                335 | 1210 |

```
tgg aac tca atc ttg ccg gaa tgg tat ccg gga gac gcc aca gtc gat    1258
Trp Asn Ser Ile Leu Pro Glu Trp Tyr Pro Gly Asp Ala Thr Val Asp
    340                 345                 350 atc ctc agc gcg gat gtc tat gca cag ggc aat gga gtgagtgcaa         1304
Ile Leu Ser Ala Asp Val Tyr Ala Gln Gly Asn Gly
355                 360                 365 agacccggg actttctgtt gacaggaaac tgacgccatc ttctag ccc atg tca      1359
                                                  Pro Met Ser acg cag tat aac cag ctg atc gaa ctg ggc aaa gac aag aaa atg att    1407
Thr Gln Tyr Asn Gln Leu Ile Glu Leu Gly Lys Asp Lys Lys Met Ile
370                 375                 380                 385 gcc gcg gcc gag gtg ggc gcg gca cct ctc cca gat ctt ttg cag gct    1455
Ala Ala Ala Glu Val Gly Ala Ala Pro Leu Pro Asp Leu Leu Gln Ala
                390                 395                 400 tat gag gcc cat tgg ctt tgg ttc act gtt tgg ggt gac tcc ttc att    1503
Tyr Glu Ala His Trp Leu Trp Phe Thr Val Trp Gly Asp Ser Phe Ile
            405                 410                 415 aac aac gcg gac tgg aac tcg ctg gac acc ctg aag aaa gtgagtttcc    1552
Asn Asn Ala Asp Trp Asn Ser Leu Asp Thr Leu Lys Lys
        420                 425                 430 gtctcctgga acaaatactt ccggaacgga actaacgcct gctag gtc tat acc agc  1609
                                                  Val Tyr Thr Ser gac tac gtt ctt acg ctg gac gag atc cag ggt tgg caa ggg tct acg    1657
Asp Tyr Val Leu Thr Leu Asp Glu Ile Gln Gly Trp Gln Gly Ser Thr
435                 440                 445                 450 ccc agc gcg acc acc acg tct agt acc act aca cct agc gcg acc acc    1705
Pro Ser Ala Thr Thr Thr Ser Ser Thr Thr Thr Pro Ser Ala Thr Thr
                455                 460                 465 act acc act acg ccc agc acc acc gct act acc gct acg ccc agc gcg    1753
Thr Thr Thr Thr Pro Ser Thr Thr Ala Thr Thr Ala Thr Pro Ser Ala
            470                 475                 480 acc acc act gcc tct ccc gtg acg tat gct gag cat tgg ggc cag tgc    1801
Thr Thr Thr Ala Ser Pro Val Thr Tyr Ala Glu His Trp Gly Gln Cys
485                 490                 495 gct ggc aaa gga tgg acc ggg ccg acc acc tgc agg ccc ccg tac act    1849
Ala Gly Lys Gly Trp Thr Gly Pro Thr Thr Cys Arg Pro Pro Tyr Thr
                500                 505                 510 tgc aag tac caa aat gat tgg tac tcg cag tgt ttg taa                1888
Cys Lys Tyr Gln Asn Asp Trp Tyr Ser Gln Cys Leu
515                 520                 525

<210> SEQ ID NO 5
<211> LENGTH: 552
<212> TYPE: PRT
<213> ORGANISM: Chaetomium virescens

<400> SEQUENCE: 5

Met Asp Lys Ile Leu Arg Tyr Phe Leu Cys Gly Ile Ile Ala Leu Ala
        -25                 -20                 -15

Gly Ala Thr Thr Ala Ala Pro Ser Tyr Gln Pro Arg Asp Pro Gly Ala
-10                  -5                 -1  1                  5

Thr Ala Arg Thr Phe Glu Ala Glu Asp Ala Thr Leu Ala Gly Thr Asn
                10                  15                  20

Val Asp Thr Ala Leu Ser Gly Phe Thr Gly Thr Gly Tyr Val Thr Gly
            25                  30                  35

Phe Asp Gln Ala Ala Asp Lys Val Thr Phe Thr Val Asp Ser Ala Ser
        40                  45                  50

Thr Glu Leu Tyr Asp Leu Ser Ile Arg Val Ala Ala Ile Tyr Gly Asp
55                  60                  65                  70
```

-continued

```
Lys Arg Thr Ser Val Val Leu Asn Gly Gly Ala Ser Ser Glu Val Tyr
                 75                  80                  85
Phe Pro Ala Gly Glu Thr Trp Thr Asn Val Ala Ala Gly Gln Leu Leu
             90                  95                 100
Leu Asn Gln Gly Ser Asn Thr Ile Asp Ile Val Ser Asn Trp Gly Trp
            105                 110                 115
Tyr Leu Ile Asp Ser Ile Thr Leu Thr Pro Ser Thr Pro Arg Pro Ala
        120                 125                 130
His Gln Ile Asn Glu Ala Pro Val Asn Ala Ala Asp Lys Asn Ala
135                 140                 145                 150
Lys Ala Leu Tyr Ser Tyr Leu Arg Ser Ile Tyr Gly Lys Lys Ile Leu
                155                 160                 165
Ser Gly Gln Gln Glu Leu Ser Leu Ser Asn Trp Ile Ala Gln Gln Thr
            170                 175                 180
Gly Lys Thr Pro Ala Leu Val Ser Val Asp Leu Met Asp Tyr Ser Pro
        185                 190                 195
Ser Arg Val Glu Arg Gly Thr Val Gly Thr Ala Val Glu Glu Ala Ile
    200                 205                 210
Gln His His Asn Arg Gly Gly Ile Val Ser Val Leu Trp His Trp Asn
215                 220                 225                 230
Ala Pro Thr Gly Leu Tyr Asp Thr Glu Glu His Arg Trp Trp Ser Gly
                235                 240                 245
Phe Tyr Thr Ser Ala Thr Asp Phe Asp Val Ala Ala Ala Leu Ser Ser
            250                 255                 260
Thr Thr Asn Ala Asn Tyr Thr Leu Leu Ile Arg Asp Ile Asp Ala Ile
            265                 270                 275
Ala Val Gln Leu Lys Arg Leu Gln Ser Ala Gly Val Pro Val Leu Phe
        280                 285                 290
Arg Pro Leu His Glu Ala Glu Gly Gly Trp Phe Trp Trp Gly Ala Lys
295                 300                 305                 310
Gly Pro Glu Pro Ala Lys Lys Leu Trp Gly Ile Leu Tyr Asp Arg Val
                315                 320                 325
Thr Asn His His Gln Ile Asn Asn Leu Leu Trp Val Trp Asn Ser Ile
            330                 335                 340
Leu Pro Glu Trp Tyr Pro Gly Asp Ala Thr Val Asp Ile Leu Ser Ala
        345                 350                 355
Asp Val Tyr Ala Gln Gly Asn Gly Pro Met Ser Thr Gln Tyr Asn Gln
        360                 365                 370
Leu Ile Glu Leu Gly Lys Asp Lys Lys Met Ile Ala Ala Ala Glu Val
375                 380                 385                 390
Gly Ala Ala Pro Leu Pro Asp Leu Leu Gln Ala Tyr Glu Ala His Trp
                395                 400                 405
Leu Trp Phe Thr Val Trp Gly Asp Ser Phe Ile Asn Asn Ala Asp Trp
            410                 415                 420
Asn Ser Leu Asp Thr Leu Lys Lys Val Tyr Thr Ser Asp Tyr Val Leu
        425                 430                 435
Thr Leu Asp Glu Ile Gln Gly Trp Gln Gly Ser Thr Pro Ser Ala Thr
        440                 445                 450
Thr Thr Ser Ser Thr Thr Thr Pro Ser Ala Thr Thr Thr Thr Thr
455                 460                 465                 470
Pro Ser Thr Thr Ala Thr Thr Ala Thr Pro Ser Ala Thr Thr Thr Ala
                475                 480                 485
```

Ser Pro Val Thr Tyr Ala Glu His Trp Gly Gln Cys Ala Gly Lys Gly
            490                 495                 500

Trp Thr Gly Pro Thr Thr Cys Arg Pro Pro Tyr Thr Cys Lys Tyr Gln
            505                 510                 515

Asn Asp Trp Tyr Ser Gln Cys Leu
    520                 525

<210> SEQ ID NO 6
<211> LENGTH: 526
<212> TYPE: PRT
<213> ORGANISM: Chaetomium virescens

<400> SEQUENCE: 6

Pro Arg Asp Pro Gly Ala Thr Ala Arg Thr Phe Glu Ala Glu Asp Ala
1               5                   10                  15

Thr Leu Ala Gly Thr Asn Val Asp Thr Ala Leu Ser Gly Phe Thr Gly
            20                  25                  30

Thr Gly Tyr Val Thr Gly Phe Asp Gln Ala Ala Asp Lys Val Thr Phe
        35                  40                  45

Thr Val Asp Ser Ala Ser Thr Glu Leu Tyr Asp Leu Ser Ile Arg Val
    50                  55                  60

Ala Ala Ile Tyr Gly Asp Lys Arg Thr Ser Val Val Leu Asn Gly Gly
65                  70                  75                  80

Ala Ser Ser Glu Val Tyr Phe Pro Ala Gly Glu Thr Trp Thr Asn Val
                85                  90                  95

Ala Ala Gly Gln Leu Leu Leu Asn Gln Gly Ser Asn Thr Ile Asp Ile
            100                 105                 110

Val Ser Asn Trp Gly Trp Tyr Leu Ile Asp Ser Ile Thr Leu Thr Pro
        115                 120                 125

Ser Thr Pro Arg Pro Ala His Gln Ile Asn Glu Ala Pro Val Asn Ala
    130                 135                 140

Ala Ala Asp Lys Asn Ala Lys Ala Leu Tyr Ser Tyr Leu Arg Ser Ile
145                 150                 155                 160

Tyr Gly Lys Lys Ile Leu Ser Gly Gln Gln Glu Leu Ser Leu Ser Asn
                165                 170                 175

Trp Ile Ala Gln Gln Thr Gly Lys Thr Pro Ala Leu Val Ser Val Asp
            180                 185                 190

Leu Met Asp Tyr Ser Pro Ser Arg Val Glu Arg Gly Thr Val Gly Thr
        195                 200                 205

Ala Val Glu Glu Ala Ile Gln His His Asn Arg Gly Gly Ile Val Ser
    210                 215                 220

Val Leu Trp His Trp Asn Ala Pro Thr Gly Leu Tyr Asp Thr Glu Glu
225                 230                 235                 240

His Arg Trp Trp Ser Gly Phe Tyr Thr Ser Ala Thr Asp Phe Asp Val
                245                 250                 255

Ala Ala Ala Leu Ser Ser Thr Thr Asn Ala Asn Tyr Thr Leu Leu Ile
            260                 265                 270

Arg Asp Ile Asp Ala Ile Ala Val Gln Leu Lys Arg Leu Gln Ser Ala
        275                 280                 285

Gly Val Pro Val Leu Phe Arg Pro Leu His Glu Ala Glu Gly Gly Trp
    290                 295                 300

Phe Trp Trp Gly Ala Lys Gly Pro Glu Pro Ala Lys Lys Leu Trp Gly
305                 310                 315                 320

Ile Leu Tyr Asp Arg Val Thr Asn His His Gln Ile Asn Asn Leu Leu
                325                 330                 335

Trp Val Trp Asn Ser Ile Leu Pro Glu Trp Tyr Pro Gly Asp Ala Thr
        340                 345                 350

Val Asp Ile Leu Ser Ala Asp Val Tyr Ala Gln Gly Asn Gly Pro Met
    355                 360                 365

Ser Thr Gln Tyr Asn Gln Leu Ile Glu Leu Gly Lys Asp Lys Lys Met
    370                 375                 380

Ile Ala Ala Ala Glu Val Gly Ala Ala Pro Leu Pro Asp Leu Leu Gln
385                 390                 395                 400

Ala Tyr Glu Ala His Trp Leu Trp Phe Thr Val Trp Gly Asp Ser Phe
                405                 410                 415

Ile Asn Asn Ala Asp Trp Asn Ser Leu Asp Thr Leu Lys Lys Val Tyr
            420                 425                 430

Thr Ser Asp Tyr Val Leu Thr Leu Asp Glu Ile Gln Gly Trp Gln Gly
        435                 440                 445

Ser Thr Pro Ser Ala Thr Thr Thr Ser Ser Thr Thr Thr Pro Ser Ala
    450                 455                 460

Thr Thr Thr Thr Thr Thr Pro Ser Thr Thr Ala Thr Thr Ala Thr Pro
465                 470                 475                 480

Ser Ala Thr Thr Thr Ala Ser Pro Val Thr Tyr Ala Glu His Trp Gly
                485                 490                 495

Gln Cys Ala Gly Lys Gly Trp Thr Gly Pro Thr Thr Cys Arg Pro Pro
            500                 505                 510

Tyr Thr Cys Lys Tyr Gln Asn Asp Trp Tyr Ser Gln Cys Leu
        515                 520                 525

<210> SEQ ID NO 7
<211> LENGTH: 42
<212> TYPE: DNA
<213> ORGANISM: Artificial Sequence
<220> FEATURE:
<223> OTHER INFORMATION: Synthetic construct

<400> SEQUENCE: 7
acacaactgg ggatccacca tgcgtttctc tctctgcgtc gg           42

<210> SEQ ID NO 8
<211> LENGTH: 38
<212> TYPE: DNA
<213> ORGANISM: Artificial Sequence
<220> FEATURE:
<223> OTHER INFORMATION: Synthetic construct

<400> SEQUENCE: 8
ccctctagat ctcgagcctt cctcctttcc tagcagct               38

<210> SEQ ID NO 9
<211> LENGTH: 47
<212> TYPE: DNA
<213> ORGANISM: Artificial Sequence
<220> FEATURE:
<223> OTHER INFORMATION: Synthetic construct

<400> SEQUENCE: 9
acacaactgg ggatccacca tggacaaaat cctcagatac tttctct     47

<210> SEQ ID NO 10
<211> LENGTH: 36
<212> TYPE: DNA
<213> ORGANISM: Artificial Sequence
<220> FEATURE:
<223> OTHER INFORMATION: Synthetic construct

```
<400> SEQUENCE: 10
ccctctagat ctcgagcatg ctttaaccgc ctgcaa                                      36

<210> SEQ ID NO 11
<211> LENGTH: 437
<212> TYPE: PRT
<213> ORGANISM: Trichoderma reesei
<220> FEATURE:
<221> NAME/KEY: mat_peptide
<222> LOCATION: (20)..(437)

<400> SEQUENCE: 11
```

| Met | Met | Met | Leu | Ser | Lys | Ser | Leu | Leu | Ser | Ala | Ala | Thr | Ala | Ala | Ser |
|-----|-----|-----|-----|-----|-----|-----|-----|-----|-----|-----|-----|-----|-----|-----|-----|
|     |     |     |     | -15 |     |     |     |     | -10 |     |     |     |     | -5  |     |

| Ala | Leu | Ala | Ala | Val | Leu | Gln | Pro | Val | Pro | Arg | Ala | Ser | Ser | Phe | Val |
|-----|-----|-----|-----|-----|-----|-----|-----|-----|-----|-----|-----|-----|-----|-----|-----|
|     | -1  | 1   |     |     |     | 5   |     |     |     |     | 10  |     |     |     |     |

| Thr | Ile | Ser | Gly | Thr | Gln | Phe | Asn | Ile | Asp | Gly | Lys | Val | Gly | Tyr | Phe |
|-----|-----|-----|-----|-----|-----|-----|-----|-----|-----|-----|-----|-----|-----|-----|-----|
|     |     | 15  |     |     |     |     | 20  |     |     |     |     | 25  |     |     |     |

| Ala | Gly | Thr | Asn | Cys | Tyr | Trp | Cys | Ser | Phe | Leu | Thr | Asn | His | Ala | Asp |
|-----|-----|-----|-----|-----|-----|-----|-----|-----|-----|-----|-----|-----|-----|-----|-----|
| 30  |     |     |     |     | 35  |     |     |     |     | 40  |     |     |     |     | 45  |

| Val | Asp | Ser | Thr | Phe | Ser | His | Ile | Ser | Ser | Ser | Gly | Leu | Lys | Val | Val |
|-----|-----|-----|-----|-----|-----|-----|-----|-----|-----|-----|-----|-----|-----|-----|-----|
|     |     |     |     | 50  |     |     |     |     | 55  |     |     |     |     | 60  |     |

| Arg | Val | Trp | Gly | Phe | Asn | Asp | Val | Asn | Thr | Gln | Pro | Ser | Pro | Gly | Gln |
|-----|-----|-----|-----|-----|-----|-----|-----|-----|-----|-----|-----|-----|-----|-----|-----|
|     |     |     | 65  |     |     |     |     | 70  |     |     |     |     | 75  |     |     |

| Ile | Trp | Phe | Gln | Lys | Leu | Ser | Ala | Thr | Gly | Ser | Thr | Ile | Asn | Thr | Gly |
|-----|-----|-----|-----|-----|-----|-----|-----|-----|-----|-----|-----|-----|-----|-----|-----|
|     |     |     | 80  |     |     |     |     | 85  |     |     |     |     | 90  |     |     |

| Ala | Asp | Gly | Leu | Gln | Thr | Leu | Asp | Tyr | Val | Val | Gln | Ser | Ala | Glu | Gln |
|-----|-----|-----|-----|-----|-----|-----|-----|-----|-----|-----|-----|-----|-----|-----|-----|
|     | 95  |     |     |     |     | 100 |     |     |     |     | 105 |     |     |     |     |

| His | Asn | Leu | Lys | Leu | Ile | Ile | Pro | Phe | Val | Asn | Asn | Trp | Ser | Asp | Tyr |
|-----|-----|-----|-----|-----|-----|-----|-----|-----|-----|-----|-----|-----|-----|-----|-----|
| 110 |     |     |     |     | 115 |     |     |     |     | 120 |     |     |     |     | 125 |

| Gly | Gly | Ile | Asn | Ala | Tyr | Val | Asn | Ala | Phe | Gly | Gly | Asn | Ala | Thr | Thr |
|-----|-----|-----|-----|-----|-----|-----|-----|-----|-----|-----|-----|-----|-----|-----|-----|
|     |     |     | 130 |     |     |     |     | 135 |     |     |     |     | 140 |     |     |

| Trp | Tyr | Thr | Asn | Thr | Ala | Ala | Gln | Thr | Gln | Tyr | Arg | Lys | Tyr | Val | Gln |
|-----|-----|-----|-----|-----|-----|-----|-----|-----|-----|-----|-----|-----|-----|-----|-----|
|     |     |     | 145 |     |     |     |     | 150 |     |     |     |     | 155 |     |     |

| Ala | Val | Val | Ser | Arg | Tyr | Ala | Asn | Ser | Thr | Ala | Ile | Phe | Ala | Trp | Glu |
|-----|-----|-----|-----|-----|-----|-----|-----|-----|-----|-----|-----|-----|-----|-----|-----|
|     | 160 |     |     |     |     | 165 |     |     |     |     | 170 |     |     |     |     |

| Leu | Gly | Asn | Glu | Pro | Arg | Cys | Asn | Gly | Cys | Ser | Thr | Asp | Val | Ile | Val |
|-----|-----|-----|-----|-----|-----|-----|-----|-----|-----|-----|-----|-----|-----|-----|-----|
| 175 |     |     |     |     | 180 |     |     |     |     | 185 |     |     |     |     |     |

| Gln | Trp | Ala | Thr | Ser | Val | Ser | Gln | Tyr | Val | Lys | Ser | Leu | Asp | Ser | Asn |
|-----|-----|-----|-----|-----|-----|-----|-----|-----|-----|-----|-----|-----|-----|-----|-----|
| 190 |     |     |     |     | 195 |     |     |     |     | 200 |     |     |     |     | 205 |

| His | Leu | Val | Thr | Leu | Gly | Asp | Glu | Gly | Leu | Gly | Leu | Ser | Thr | Gly | Asp |
|-----|-----|-----|-----|-----|-----|-----|-----|-----|-----|-----|-----|-----|-----|-----|-----|
|     |     |     | 210 |     |     |     |     | 215 |     |     |     |     | 220 |     |     |

| Gly | Ala | Tyr | Pro | Tyr | Thr | Tyr | Gly | Glu | Gly | Thr | Asp | Phe | Ala | Lys | Asn |
|-----|-----|-----|-----|-----|-----|-----|-----|-----|-----|-----|-----|-----|-----|-----|-----|
|     |     |     | 225 |     |     |     |     | 230 |     |     |     |     | 235 |     |     |

| Val | Gln | Ile | Lys | Ser | Leu | Asp | Phe | Gly | Thr | Phe | His | Leu | Tyr | Pro | Asp |
|-----|-----|-----|-----|-----|-----|-----|-----|-----|-----|-----|-----|-----|-----|-----|-----|
|     | 240 |     |     |     |     | 245 |     |     |     |     | 250 |     |     |     |     |

| Ser | Trp | Gly | Thr | Asn | Tyr | Thr | Trp | Gly | Asn | Gly | Trp | Ile | Gln | Thr | His |
|-----|-----|-----|-----|-----|-----|-----|-----|-----|-----|-----|-----|-----|-----|-----|-----|
| 255 |     |     |     |     | 260 |     |     |     |     | 265 |     |     |     |     |     |

| Ala | Ala | Ala | Cys | Leu | Ala | Ala | Gly | Lys | Pro | Cys | Val | Phe | Glu | Glu | Tyr |
|-----|-----|-----|-----|-----|-----|-----|-----|-----|-----|-----|-----|-----|-----|-----|-----|
| 270 |     |     |     |     | 275 |     |     |     |     | 280 |     |     |     |     | 285 |

| Gly | Ala | Gln | Gln | Asn | Pro | Cys | Thr | Asn | Glu | Ala | Pro | Trp | Gln | Thr | Thr |
|-----|-----|-----|-----|-----|-----|-----|-----|-----|-----|-----|-----|-----|-----|-----|-----|
|     |     |     |     | 290 |     |     |     |     | 295 |     |     |     |     | 300 |     |

| Ser | Leu | Thr | Thr | Arg | Gly | Met | Gly | Gly | Asp | Met | Phe | Trp | Gln | Trp | Gly |
|-----|-----|-----|-----|-----|-----|-----|-----|-----|-----|-----|-----|-----|-----|-----|-----|
|     |     |     | 305 |     |     |     |     | 310 |     |     |     |     | 315 |     |     |

-continued

```
Asp Thr Phe Ala Asn Gly Ala Gln Ser Asn Ser Asp Pro Tyr Thr Val
        320             325             330

Trp Tyr Asn Ser Ser Asn Trp Gln Cys Leu Val Lys Asn His Val Asp
    335             340             345

Ala Ile Asn Gly Gly Thr Thr Thr Pro Pro Pro Val Ser Ser Thr Thr
350             355             360             365

Thr Thr Ser Ser Arg Thr Ser Ser Thr Pro Pro Pro Pro Gly Gly Ser
                370             375             380

Cys Ser Pro Leu Tyr Gly Gln Cys Gly Gly Ser Gly Tyr Thr Gly Pro
            385             390             395

Thr Cys Cys Ala Gln Gly Thr Cys Ile Tyr Ser Asn Tyr Trp Tyr Ser
        400             405             410

Gln Cys Leu Asn Thr
    415
```

POLYPEPTIDES HAVING MANNANASE ACTIVITY AND POLYNUCLEOTIDES ENCODING SAME

REFERENCE TO A SEQUENCE LISTING

This application contains a Sequence Listing in computer readable form, which is incorporated herein by reference.

BACKGROUND OF THE INVENTION

Field of the Invention

The present invention relates to polypeptides having mannanase activity, catalytic domains, and carbohydrate binding modules, and polynucleotides encoding the polypeptides, catalytic domains, and carbohydrate binding modules. The invention also relates to nucleic acid constructs, vectors, and host cells comprising the polynucleotides as well as methods of producing and using the polypeptides, catalytic domains, and carbohydrate binding modules.

Description of the Related Art

Mannans are a type of hemicellulose representing up to 25% of wood dry weight in softwoods, but are also found in other plant material, especially in a variety of seeds. Mannans are polysaccharides with a backbone of β-1,4-linked D-mannopyranosyl residues, which can contain galactose or acetyl substitutions and may have glucose residues in the backbone. The main enzyme type participating in the degradation of mannans are endo-1,4-β-mannanases (EC 3.2.1.78), which hydrolyze the internal glycoside bonds in the mannan backbone.

Thus it could be advantageous to use endomannanases in applications where mannan needs to be degraded. Examples of where mannanases could be used are in the production of bioethanol from softwood (Várnai et al, (2011) "Synergistic action of xylanase and mannanase improves the total hydrolysis of softwood", *Bioresource tech.*, 102(19), pp. 9096-104) and palm kernel press cake (Jørgensen et al, (2010) "Production of ethanol and feed by high dry matter hydrolysis and fermentation of palm kernel press cake", *Applied Biochem. Biotech.*, 161(1-8), pp. 318-32), for the improvement of animal feed (Cai, et al, (2011), "Acidic β-mannanase from *Penicillium pinophilum* C1: Cloning, characterization and assessment of its potential for animal feed application", *J. Biosci. Bioeng.*, 112(6), pp. 551-557) and in the hydrolysis of coffee extract (Nunes et al, (2006), "Characterization of Galactomannan Derivatives in Roasted Coffee Beverages", *J. Agricultural Food Chem.*, 54(9), pp. 3428-3439). Furthermore, guar gum is used in many food products, and so mannanases could be used in detergents to remove mannan containing stains.

According to CAZy (www.cazy.org), endo-1,4-β-mannanases can be found in glycoside hydrolase families 5, 26 and 113. Couturier et al. have reported a GH26 mannanase from *Podospora anserina* having 56.1% and 76.4% identity to SEQ ID NO: 3 and 6 respectively in (2013), "Structural and Biochemical Analyses of Glycoside Hydrolase Families 5 and 26-(1,4)-Mannanases from *Podospora anserina* Reveal Differences upon Manno-oligosaccharide Catalysis", J. Biol. Chem., 288(20): 14624-14635.

However, there are currently no reports in the literature describing that GH26 mannanases can be used for degrading highly substituted mannan. Furthermore, there are very few examples of fungal GH26 mannanases. The present invention provides polypeptides having mannanase activity and polynucleotides encoding the polypeptides that are highly active in degrading different types of mannan, and therefore could be used in the aforementioned applications.

SUMMARY OF THE INVENTION

The present invention relates to polypeptides having mannanase activity selected from the group consisting of:

(a) a polypeptide having at least 60% sequence identity to SEQ ID NO: 3 or the mature polypeptide of SEQ ID NO: 2;

(b) a polypeptide having at least 81% sequence identity to SEQ ID NO: 6 or the mature polypeptide of SEQ ID NO: 5;

(c) a polypeptide encoded by a polynucleotide that hybridizes under very low, low, medium, medium-high, high, or very high stringency conditions with:
  (i) the mature polypeptide coding sequence of SEQ ID NO: 1,
  (ii) the cDNA sequence thereof, or
  (iii) the full-length complement of (i) or (ii);

(d) a polypeptide encoded by a polynucleotide that hybridizes under medium, medium-high, high, or very high stringency conditions with:
  (i) the mature polypeptide coding sequence of SEQ ID NO: 4,
  (ii) the cDNA sequence thereof, or
  (iii) the full-length complement of (i) or (ii);

(e) a polypeptide encoded by a polynucleotide having at least 60% sequence identity to the mature polypeptide coding sequence of SEQ ID NO: 1 or the cDNA sequence thereof;

(f) a polypeptide encoded by a polynucleotide having at least 81% sequence identity to the mature polypeptide coding sequence of SEQ ID NO: 4 or the cDNA sequence thereof;

(g) a variant of SEQ ID NO: 3 or the mature polypeptide of SEQ ID NO: 2 comprising a substitution, deletion, and/or insertion at one or more (e.g., several) positions;

(h) a variant of SEQ ID NO: 6 or the mature polypeptide of SEQ ID NO: 5 comprising a substitution, deletion, and/or insertion at one or more (e.g., several) positions; and (i) a fragment of the polypeptide of (a), (b), (c), (d), (e), (f), (g) or (h) that has mannanase activity.

The present invention also relates to polypeptides comprising a catalytic domain selected from the group consisting of:

(a) a catalytic domain having at least 65% sequence identity to amino acids 128 to 446 of SEQ ID NO: 2;

(b) a catalytic domain having at least 87% sequence identity to amino acids 135 to 448 of SEQ ID NO: 5;

(c) a catalytic domain encoded by a polynucleotide that hybridizes under very low, low, medium, medium-high, high, or very high stringency conditions with:
  (i) nucleotides 490 to 1446 of SEQ ID NO: 1,
  (ii) the cDNA sequence thereof, or
  (iii) the full-length complement of (i) or (ii);

(d) a catalytic domain encoded by a polynucleotide that hybridizes under medium-high, high, or very high stringency conditions with:
  (i) nucleotides 599 to 1651 of SEQ ID NO: 4,
  (ii) the cDNA sequence thereof, or
  (iii) the full-length complement of (i) or (ii);

(e) a catalytic domain encoded by a polynucleotide having at least 65% sequence identity to nucleotides 490 to 1446 of SEQ ID NO: 1 or the cDNA sequence thereof;

(f) a catalytic domain encoded by a polynucleotide having at least 87% sequence identity to nucleotides 599 to 1651 of SEQ ID NO: 4 or the cDNA sequence thereof;

(g) a variant of amino acids 128 to 446 of SEQ ID NO: 2 comprising a substitution, deletion, and/or insertion at one or more (e.g., several) positions; and (h) a variant of amino acids 135 to 448 of SEQ ID NO: 5 comprising a substitution, deletion, and/or insertion at one or more (e.g., several) positions; and (i) a fragment of the catalytic domain of (a), (b), (c), (d), (e), (f), (g) or (h) that has mannanase activity.

The present invention also relates to polypeptides comprising a carbohydrate binding module operably linked to a catalytic domain, wherein the binding module is selected from the group consisting of:

(a) a carbohydrate binding module having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 1 to 124 of SEQ ID NO: 2;

(b) a carbohydrate binding module having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 508 to 541 of SEQ ID NO: 2;

(c) a carbohydrate binding module having at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 1 to 130 of SEQ ID NO: 5;

(d) a carbohydrate binding module having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 492 to 526 of SEQ ID NO: 5;

(e) a carbohydrate binding module encoded by a polynucleotide that hybridizes under very low, low, medium, medium-high, high, or very high stringency conditions with:
  (i) nucleotides 61 to 480 of SEQ ID NO: 1,
  (ii) the cDNA sequence thereof, or
  (iii) the full-length complement of (i) or (ii);

(f) a carbohydrate binding module encoded by a polynucleotide that hybridizes under medium, medium-high, high, or very high stringency conditions with:
  (i) nucleotides 1630 to 1731 of SEQ ID NO: 1,
  (ii) the cDNA sequence thereof, or
  (iii) the full-length complement of (i) or (ii);

(g) a carbohydrate binding module encoded by a polynucleotide that hybridizes under medium, medium-high, high, or very high stringency conditions with:
  (i) nucleotides 82 to 586 of SEQ ID NO: 4,
  (ii) the cDNA sequence thereof, or
  (iii) the full-length complement of (i) or (ii);

(h) a carbohydrate binding module encoded by a polynucleotide that hybridizes under medium, medium-high, high, or very high stringency conditions with:
  (i) nucleotides 1781 to 1885 of SEQ ID NO: 4,
  (ii) the cDNA sequence thereof, or
  (iii) the full-length complement of (i) or (ii);

(i) a carbohydrate binding module encoded by a polynucleotide having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 61 to 480 of SEQ ID NO: 1 or the cDNA sequence thereof;

(j) a carbohydrate binding module encoded by a polynucleotide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 1630 to 1731 of SEQ ID NO: 1 or the cDNA sequence thereof;

(k) a carbohydrate binding module encoded by a polynucleotide having at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 82 to 586 of SEQ ID NO: 4 or the cDNA sequence thereof;

(l) a carbohydrate binding module encoded by a polynucleotide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 1781 to 1885 of SEQ ID NO: 4 or the cDNA sequence thereof;

(m) a variant of amino acids 1 to 124 of SEQ ID NO: 2 comprising a substitution, deletion, and/or insertion at one or more (e.g., several) positions; and (n) a variant of amino acids 508 to 541 of SEQ ID NO: 2 comprising a substitution, deletion, and/or insertion at one or more (e.g., several) positions; and (o) a variant of amino acids 1 to 130 of SEQ ID NO: 5 comprising a substitution, deletion, and/or insertion at one or more (e.g., several) positions; and (p) a variant of amino acids 492 to 526 of SEQ ID NO: 5 comprising a substitution, deletion, and/or insertion at one or more (e.g., several) positions; and (q) a fragment of the carbohydrate binding module of (a), (b), (c), (d), (e), (f), (g), (h), (i), (j), (k), (l), (m), (n), (o) or (p) that has carbohydrate binding activity.

The present invention also relates to compositions comprising the polypeptide of the present invention and the use of polypeptides of the present invention in degrading mannan, controlling the viscosity of drilling fluids, for washing or cleaning a textile and/or a hard surface; methods for degrading mannan comprising applying a composition comprising the polypeptide of the present invention to the mannan; methods for producing a coffee extract using a polypeptide of the present invention; and processes for degrading a cellulosic material, for producing a fermentation product and for fermenting a cellulosic material.

The present invention also relates to polynucleotides encoding the polypeptides of the present invention; nucleic acid constructs; recombinant expression vectors; recombinant host cells comprising the polynucleotides; and methods of producing the polypeptides.

Furthermore, the invention relates to whole broth formulations or cell culture compositions comprising the polypeptides.

The present invention also relates to use of the polypeptide according the first aspect for preventing, reducing or removing a biofilm from an item.

BRIEF DESCRIPTION OF THE DRAWINGS

FIG. 1. The results show that the GH26 mannanases convert a significantly higher amount of guar gum galactomannan to mannan than the known GH5 mannanase from *Trichoderma reesei*.

OVERVIEW OF SEQUENCE LISTING

SEQ ID NO: 1 is the DNA sequence of the mannanase as isolated from *Ascobolus stictoideus*.
SEQ ID NO: 2 is the amino acid sequence as deduced from SEQ ID NO: 1.
SEQ ID NO: 3 is the amino acid sequence of the mature mannanase isolated from *Ascobolus stictoideus*.
SEQ ID NO: 4 is the DNA sequence of the mannanase as isolated from *Chaetomium virescens*.
SEQ ID NO: 5 is the amino acid sequence as deduced from SEQ ID NO: 4.
SEQ ID NO: 6 is the amino acid sequence of the mature mannanase isolated from *Chaetomium virescens*.
SEQ ID NO: 7 is the primer F-P335AW.
SEQ ID NO: 8 is the primer R-P335AW.
SEQ ID NO: 9 is the primer F-P335AV.
SEQ ID NO: 10 is the primer R-P335AV.
SEQ ID NO: 11 the amino acid sequence of a GH5 mannanase from *Trichoderma reesei* (SWISSPROT: Q99036).

Definitions

Auxiliary Activity 9: The term "Auxiliary Activity 9" or "AA9" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Beta-1,3-galactanase: The term "beta-1,3-galactanase" means an enzyme which specifically hydrolyses beta-1,3-galactan and beta-1,3-galactooligosaccharides. The enzyme may have primarily endo-beta-1,3-galactanase activity (EC 3.2.1.181) or it may have exo activity (EC 3.2.1.145). The beta-1,3-galactanase activity may be quantified using the Reducing sugar assay (PAH-BAH assay) using the colorimetric assay developed by Lever (1972), *Anal. Biochem.* 47: 273-279, 1972.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Biofilm: The term "biofilm" means any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One effect of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp.

Carbohydrate binding module: The term "carbohydrate binding module" means the region within a carbohydrate-active enzyme that provides carbohydrate-binding activity (Boraston et al., 2004, *Biochem. J.* 383: 769-781). A majority of known carbohydrate binding modules (CBMs) are contiguous amino acid sequences with a discrete fold. The carbohydrate binding module (CBM) is typically found either at the N-terminal or at the C-terminal extremity of an enzyme. Some CBMs are known to have specificity for cellulose.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman NQ1 filter paper, microcrystalline cellulose, bacterial cellulose, algal cellulose, cotton, pretreated lignocellulose, etc. The most common total cellulolytic activity assay is the filter paper assay using Whatman NQ1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In one aspect, the cellulosic material is any biomass material. In another aspect, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is arundo, bagasse, bamboo, corn cob, corn fiber, corn stover, miscanthus, rice straw, switchgrass, or wheat straw.

In another embodiment, the cellulosic material is aspen, eucalyptus, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Deep cleaning: The term "deep cleaning" meant disruption or removal of a biofilm or components of a biofilm such as polysaccharides, proteins, DNA, soil or other components present in the biofilm.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to containing a GH9 endoglucanase of the invention and/or xanthan lyase of the invention, the detergent formulation may contain one or more additional enzymes (such as proteases, amylases, lipases, cutinases, cellulases, endoglucanases, xyloglucanases, pectinases, pectin lyases, xanthanases, peroxidaes, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide or a catalytic or carbohydrate binding module having one or more (e.g., several) amino acids absent from the amino and/or carboxyl terminus of a mature polypeptide or domain; wherein the fragment has mannanase or carbohydrate binding activity. In one aspect, a fragment contains at least 521 amino acid residues (e.g., amino acids 11 to 531 of SEQ ID NO: 2) or at least 531 amino acid residues (e.g., amino acids 6 to 536 of SEQ ID NO: 2) wherein the fragment has mannanase activity. In another aspect, a fragment contains at least 506 amino acid residues (e.g., amino acids 11 to 516 of SEQ ID NO: 5) or at least 516 amino acid residues (e.g., amino acids 6 to 521 of SEQ ID NO: 5) wherein the fragment has mannanase activity.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). A fermentation broth produced by culturing a recombinant host cell expressing the polynucleotide of the invention will comprise the polypeptide of the invention in an isolated form.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mannanase: The term "mannanase" means a polypeptide having mannan endo-1,4-beta-mannosidase activity (EC 3.2.1.78) that catalyzes the hydrolysis of 1,4-β-D-mannosidic linkages in mannans, galactomannans and glucomannans. Alternative names of mannan endo-1,4-beta-mannosidase are 1,4-β-D-mannan mannanohydrolase; endo-1,4-β-mannanase; endo-β-1,4-mannase; β-mannanase B; β-1,4-mannan 4-mannanohydrolase; endo-β-mannanase; and β-D-mannanase. For purposes of the present invention, mannanase activity may be determined using the Reducing End Assay as described in the experimental section. In one aspect, the polypeptides of the present invention have at least 20%, e.g., at least 40%, at least 50%, at least 60%, at least 70%, at least 80%, at least 90%, at least 95%, or at least 100% of the mannanase activity of the mature polypeptide of SEQ ID NO: 2 and/or the mature polypeptide of SEQ ID NO: 5.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 541 of SEQ ID NO: 2 or amino acids 1 to 541 of SEQ ID NO: 3. Amino acids 1 to 20 of SEQ ID NO: 2 are a signal peptide. In one aspect, the mature polypeptide is amino acids 121 to 541 of SEQ ID NO: 2. In another aspect, the mature polypeptide is amino acids 1 to 525 of SEQ ID NO: 5 or amino acids 1 to 525 of SEQ ID NO: 6 Amino acids −26 to −1 of SEQ ID NO: 5 are a signal peptide.

In a preferred aspect, the mature polypeptide is amino acids 1 to 526 of SEQ ID NO: 5 or amino acids 1 to 526 of SEQ ID NO: 6

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having mannanase activity. In one aspect, the mature polypeptide coding sequence is nucleotides 61 to 1731 of SEQ ID NO: 1 or the cDNA sequence thereof based on the SignalP (Nielsen et al., 1997, supra) program that predicts nucleotides 1 to 60 of SEQ ID NO: 1 encode a signal peptide. In another aspect, the mature polypeptide coding sequence is nucleotides 79 to 1885 of SEQ ID NO: 4 or the cDNA sequence thereof based on the SignalP (Nielsen et al., 1997, supra) program that predicts nucleotides 1 to 63 of SEQ ID NO: 1 encode a signal peptide.

Malodor: The term "malodor" is meant an odor which is not desired on clean items. The cleaned item should smell fresh and clean without malodors adhered to the item. One example of malodor is compounds with an unpleasant smell, which may be produced by microorganisms. Another example is sweat or body odor adheringed to an item which has been in contact with humans or animals. Another example of malodor can be the smell from spices, for example curry or other exotic spices adheringed to an item such as a piece of textile. One way of measuring the ability of an item to adhere malodor is by using the Malodor Assay.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/
(Length of Alignment−
Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 1.6×SSC, 0.2% SDS at 60° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 0.8×SSC, 0.2% SDS at 60° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 0.8×SSC, 0.2% SDS at 65° C.

The term "medium-high stringency conditions" means for probes of at least 100 nucleotides in length, prehybridization and hybridization at 42° C. in 5×SSPE, 0.3% SDS, 200 micrograms/mi sheared and denatured salmon sperm DNA, and 35% formamide, following standard Southern blotting procedures for 12 to 24 hours. The carrier material is finally washed three times each for 15 minutes using 0.4×SSC, 0.2% SDS at 65° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 0.2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having mannanase activity. In one aspect, a subsequence contains at least 1611 nucleotides (e.g., nucleotides 91 to 1701 of SEQ ID NO: 1 or the cDNA sequence thereof) or at least 1641 nucleotides (e.g., nucleotides 76 to 1716 of SEQ ID NO: 1 or the cDNA sequence thereof). In another aspect, a subsequence contains at least 1747 nucleotides (e.g., nucleotides 109 to 1855 of SEQ ID NO: 4 or the cDNA sequence thereof) or at least 1777 nucleotides (e.g., nucleotides 94 to 1870 of SEQ ID NO: 4 or the cDNA sequence thereof).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the mannanase activity of the polypeptide of SEQ ID NO: 3, SEQ ID NO: 6, or the mature polypeptide of SEQ ID NO: 2 or SEQ ID NO: 5.

DETAILED DESCRIPTION OF THE INVENTION

Polypeptides Having Mannanase Activity

The present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have mannanase activity.

The present invention further relates to polypeptides having a sequence identity to SEQ ID NO: 3 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%, which have mannanase activity.

In an embodiment, the polypeptides have at least 70% identity to SEQ ID NO: 3 or the mature polypeptide of SEQ ID NO: 2.

In an embodiment, the polypeptides have at least 75% identity to SEQ ID NO: 3 or the mature polypeptide of SEQ ID NO: 2.

In an embodiment, the polypeptides have at least 80% identity to SEQ ID NO: 3 or the mature polypeptide of SEQ ID NO: 2.

In an embodiment, the polypeptides have at least 81% identity to SEQ ID NO: 3 or the mature polypeptide of SEQ ID NO: 2.

In an embodiment, the polypeptides have at least 82% identity to SEQ ID NO: 3 or the mature polypeptide of SEQ ID NO: 2.

In an embodiment, the polypeptides have at least 83% identity to SEQ ID NO: 3 or the mature polypeptide of SEQ ID NO: 2.

In an embodiment, the polypeptides have at least 84% identity to SEQ ID NO: 3 or the mature polypeptide of SEQ ID NO: 2.

In an embodiment, the polypeptides have at least 85% identity to SEQ ID NO: 3 or the mature polypeptide of SEQ ID NO: 2.

In an embodiment, the polypeptides have at least 86% identity to SEQ ID NO: 3 or the mature polypeptide of SEQ ID NO: 2.

In an embodiment, the polypeptides have at least 87% identity to SEQ ID NO: 3 or the mature polypeptide of SEQ ID NO: 2.

In an embodiment, the polypeptides have at least 88% identity to SEQ ID NO: 3 or the mature polypeptide of SEQ ID NO: 2.

In an embodiment, the polypeptides have at least 89% identity to SEQ ID NO: 3 or the mature polypeptide of SEQ ID NO: 2.

In an embodiment, the polypeptides have at least 90% identity to SEQ ID NO: 3 or the mature polypeptide of SEQ ID NO: 2.

In an embodiment, the polypeptides have at least 91% identity to SEQ ID NO: 3 or the mature polypeptide of SEQ ID NO: 2.

In an embodiment, the polypeptides have at least 92% identity to SEQ ID NO: 3 or the mature polypeptide of SEQ ID NO: 2.

In an embodiment, the polypeptides have at least 93% identity to SEQ ID NO: 3 or the mature polypeptide of SEQ ID NO: 2.

In an embodiment, the polypeptides have at least 94% identity to SEQ ID NO: 3 or the mature polypeptide of SEQ ID NO: 2.

In an embodiment, the polypeptides have at least 95% identity to SEQ ID NO: 3 or the mature polypeptide of SEQ ID NO: 2.

In an embodiment, the polypeptides have at least 96% identity to SEQ ID NO: 3 or the mature polypeptide of SEQ ID NO: 2.

In an embodiment, the polypeptides have at least 97% identity to SEQ ID NO: 3 or the mature polypeptide of SEQ ID NO: 2.

In an embodiment, the polypeptides have at least 98% identity to SEQ ID NO: 3 or the mature polypeptide of SEQ ID NO: 2.

In an embodiment, the polypeptides have at least 99% identity to SEQ ID NO: 3 or the mature polypeptide of SEQ ID NO: 2.

In one aspect, the polypeptides differ by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 3. In another aspect, the polypeptides differ by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 2.

In an embodiment, the polypeptide has been isolated. A polypeptide of the present invention preferably comprises or consists of the amino acid sequence of SEQ ID NO: 2 or SEQ ID NO: 3 or an allelic variant thereof; or is a fragment thereof having mannanase activity. In another aspect, the polypeptide comprises or consists of SEQ ID NO: 3 or the mature polypeptide of SEQ ID NO: 2. In another aspect, the polypeptide comprises or consists of amino acids 1 to 541 of SEQ ID NO: 2 or amino acids 1 to 541 of SEQ ID NO: 3.

The present invention further relates to polypeptides having a sequence identity to the mature polypeptide of SEQ ID NO: 4 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%, which have mannanase activity.

The present invention further relates to polypeptides having a sequence identity to SEQ ID NO: 5 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%, which have mannanase activity.

In an embodiment, the polypeptides have at least 82% identity to SEQ ID NO: 6 or the mature polypeptide of SEQ ID NO: 5.

In an embodiment, the polypeptides have at least 83% identity to SEQ ID NO: 6 or the mature polypeptide of SEQ ID NO: 5.

In an embodiment, the polypeptides have at least 84% identity to SEQ ID NO: 6 or the mature polypeptide of SEQ ID NO: 5.

In an embodiment, the polypeptides have at least 85% identity to SEQ ID NO: 6 or the mature polypeptide of SEQ ID NO: 5.

In an embodiment, the polypeptides have at least 86% identity to SEQ ID NO: 6 or the mature polypeptide of SEQ ID NO: 5.

In an embodiment, the polypeptides have at least 87% identity to SEQ ID NO: 6 or the mature polypeptide of SEQ ID NO: 5.

In an embodiment, the polypeptides have at least 88% identity to SEQ ID NO: 6 or the mature polypeptide of SEQ ID NO: 5.

In an embodiment, the polypeptides have at least 89% identity to SEQ ID NO: 6 or the mature polypeptide of SEQ ID NO: 5.

In an embodiment, the polypeptides have at least 90% identity to SEQ ID NO: 6 or the mature polypeptide of SEQ ID NO: 5.

In an embodiment, the polypeptides have at least 91% identity to SEQ ID NO: 6 or the mature polypeptide of SEQ ID NO: 5.

In an embodiment, the polypeptides have at least 92% identity to SEQ ID NO: 6 or the mature polypeptide of SEQ ID NO: 5.

In an embodiment, the polypeptides have at least 93% identity to SEQ ID NO: 6 or the mature polypeptide of SEQ ID NO: 5.

In an embodiment, the polypeptides have at least 94% identity to SEQ ID NO: 6 or the mature polypeptide of SEQ ID NO: 5.

In an embodiment, the polypeptides have at least 95% identity to SEQ ID NO: 6 or the mature polypeptide of SEQ ID NO: 5.

In an embodiment, the polypeptides have at least 96% identity to SEQ ID NO: 6 or the mature polypeptide of SEQ ID NO: 5.

In an embodiment, the polypeptides have at least 97% identity to SEQ ID NO: 6 or the mature polypeptide of SEQ ID NO: 5.

In an embodiment, the polypeptides have at least 98% identity to SEQ ID NO: 6 or the mature polypeptide of SEQ ID NO: 5.

In an embodiment, the polypeptides have at least 99% identity to SEQ ID NO: 6 or the mature polypeptide of SEQ ID NO: 5.

In one aspect, the polypeptides differ by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 6. In another aspect, the polypeptides differ by no more than thirty amino acids, e.g., by twentyfive amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the mature polypeptide of SEQ ID NO: 5.

In an embodiment, the polypeptide has been isolated. A polypeptide of the present invention preferably comprises or consists of the amino acid sequence of SEQ ID NO: 5 or SEQ ID NO: 6 or an allelic variant thereof; or is a fragment thereof having mannanase activity. In another aspect, the polypeptide comprises or consists of SEQ ID NO: 6 or the mature polypeptide of SEQ ID NO: 5. In another aspect, the polypeptide comprises or consists of amino acids 1 to 541 of SEQ ID NO: 5 or amino acids 1 to 541 of SEQ ID NO: 6.

In another embodiment, the present invention relates to a polypeptide having mannanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.). In an embodiment, the polypeptide has been isolated.

In another embodiment, the present invention relates to a polypeptide having mannanase activity encoded by a polynucleotide that hybridizes under medium stringency conditions, medium-high stringency conditions, high stringency conditions, or very high stringency conditions with (i) the mature polypeptide coding sequence of SEQ ID NO: 4, (ii) the cDNA sequence thereof, or (iii) the full-length complement of (i) or (ii) (Sambrook et al., 1989, *Molecular Cloning, A Laboratory Manual,* 2d edition, Cold Spring Harbor, N.Y.). In an embodiment, the polypeptide has been isolated.

The polynucleotide of SEQ ID NO: 1, SEQ ID NO: 4 or a subsequence thereof, as well as the polypeptide of SEQ ID NO: 2, SEQ ID NO: 3, SEQ ID NO: 5 or SEQ ID NO: 6 or a fragment thereof, may be used to design nucleic acid probes to identify and clone DNA encoding polypeptides having mannanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having mannanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 4 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the cDNA sequence thereof, (iv) the full-length complement thereof; or (v) a subsequence thereof; under very low to very high stringency conditions or to (i) SEQ ID NO: 4; (ii) the mature polypeptide coding sequence of SEQ ID NO: 4; (iii) the cDNA sequence thereof, (iv) the full-length complement thereof; or (v) a subsequence thereof; under medium to very high stringency conditions. Molecules to which the nucleic acid probe hybridizes under these conditions can be detected using, for example, X-ray film or any other detection means known in the art.

In one aspect, the nucleic acid probe is nucleotides 91 to 1701 or nucleotides 76 to 1716 of SEQ ID NO: 1 or the cDNA sequence thereor. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1 or the cDNA sequence thereof. In another aspect, the nucleic acid probe is nucleotides 109 to 1885 or nucleotides 94 to 1870 of SEQ ID NO: 4 or the cDNA sequence thereor. In another aspect, the nucleic acid probe is a polynucleotide that encodes the polypeptide of SEQ ID NO: 5; the mature polypeptide thereof; or a fragment thereof. In another aspect, the nucleic acid probe is SEQ ID NO: 4 or the cDNA sequence thereof.

In another embodiment, the present invention relates to a polypeptide having mannanase activity encoded by a polynucleotide having a sequence identity to the mature polypeptide coding sequence of SEQ ID NO: 1 of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In a further embodiment, the polypeptide has been isolated.

In another embodiment, the present invention relates to a polypeptide having mannanase activity encoded by a polynucleotide having a sequence identity to the mature polypeptide coding sequence of SEQ ID NO: 4 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In a further embodiment, the polypeptide has been isolated.

In another embodiment, the present invention relates to variants of SEQ ID NO: 3 or the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. In an embodiment, the number of amino acid substitutions, deletions and/or insertions introduced into SEQ ID NO: 3 is up to 10, e.g., 1, 2, 3, 4, 5, 6, 7, 8, 9, or 10. In another embodiment, the present invention relates to variants of SEQ ID NO: 6 or the mature polypeptide of SEQ ID NO: 5 comprising a substitution, deletion, and/or insertion at one or more (e.g., several) positions. In an embodiment, the number of amino acid substitutions, deletions and/or insertions introduced into the mature polypeptide of SEQ ID NO: 5 is up to 10, e.g., 1, 2, 3, 4, 5, 6, 7, 8, 9, or 10. In an embodiment, the number of amino acid substitutions, deletions and/or insertions introduced into SEQ ID NO: 6 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for mannanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. Essential amino acids are located at positions Glu293 and Glu386 in the sequence of amino acids 1 to 541 of SEQ ID NO: 2 or SEQ ID NO: 3 and at positions Glu299 and Glu389 in the sequence of amino acids 1 to 525 of SEQ ID NO: 5 or SEQ ID NO: 6.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Mannanase Activity

A polypeptide having mannanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a polypeptide having mannanase activity from within a phylum such as Ascomycota. In one aspect, the polypeptide is a mannanase from a fungus of the class Pezizomycetes, such as from the order Pezizales, or from the family Ascobolaceae, or from the genus *Ascobolus*, or from the species *Ascobolus stictoideus*.

In another aspect, the polypeptide may be a polypeptide having mannanase activity from within a phylum such as Ascomycota. In one aspect, the polypeptide is a mannanase from a fungus of the class Sordariomycetes, such as from the order Sordariales, or from the family Chaetomiaceae, or from the genus *Chaetomium*, or from the species *Chaetomium virescens*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 128 to 446 of SEQ ID NO: 2 of at least 65%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% In one aspect, the catalytic domains comprise amino acid sequences that differ by up to 10 amino acids, e.g., 1, 2, 3, 4, 5, 6, 7, 8, 9, or 10, from amino acids 128 to 446 of SEQ ID NO: 2.

The catalytic domain preferably comprises or consists of amino acids 128 to 446 of SEQ ID NO: 2 or an allelic variant thereof; or is a fragment thereof having mannanase activity.

In another embodiment, the present invention also relates to catalytic domains encoded by polynucleotides that hybridize under very low stringency conditions, low stringency conditions, medium stringency conditions, medium-high stringency conditions, high stringency conditions, or very high stringency conditions (as defined above) with (i) the nucleotides 490 to 1446 of SEQ ID NO: 1, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 490 to 1446 of SEQ ID NO: 1 or the cDNA sequence thereof, of at least 65%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%

In another embodiment, the present invention also relates to catalytic domain variants of amino acids 128 to 446 of SEQ ID NO: 2 comprising a substitution, deletion, and/or insertion at one or more (e.g., several) positions. In one aspect, the number of amino acid substitutions, deletions and/or insertions introduced into the sequence of amino acids 128 to 446 of SEQ ID NO: 2 is up to 10, e.g., 1, 2, 3, 4, 5, 6, 8, 9, or 10.

In a second embodiment, the present invention also relates to catalytic domains having a sequence identity to amino acids 135 to 448 of SEQ ID NO: 5 of at least 87%, e.g., at least 88%, at least 89%, at least 90%, at least 91%, at least 92%, at least 93%, at least 94%, at least 95%, at least 96%, at least 97%, at least 98%, at least 99% or 100% In one aspect, the catalytic domains comprise amino acid sequences that differ by up to 10 amino acids, e.g., 1, 2, 3, 4, 5, 6, 7, 8, 9, or 10, from amino acids 135 to 448 of SEQ ID NO: 5.

The catalytic domain preferably comprises or consists of amino acids 128 to 446 of SEQ ID NO: 5 or an allelic variant thereof; or is a fragment thereof having mannanase activity.

In another embodiment, the present invention also relates to catalytic domains encoded by polynucleotides that hybridize under medium-high stringency conditions, high stringency conditions, or very high stringency conditions (as defined above) with (i) the nucleotides 599 to 1651 of SEQ ID NO: 4, (ii) the cDNA sequence thereof, or (iii) the full-length complement of (i) or (ii) (Sambrook et al., 1989, supra).

In another embodiment, the present invention also relates to catalytic domains encoded by polynucleotides having a sequence identity to nucleotides 599 to 1651 of SEQ ID NO: 4 or the cDNA sequence thereof, of at least 65%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%

In another embodiment, the present invention also relates to catalytic domain variants of amino acids 135 to 448 of SEQ ID NO: 5 comprising a substitution, deletion, and/or insertion at one or more (e.g., several) positions. In one aspect, the number of amino acid substitutions, deletions and/or insertions introduced into the sequence of amino acids 135 to 448 of SEQ ID NO: 5 is up to 10, e.g., 1, 2, 3, 4, 5, 6, 8, 9, or 10.

Binding Domains

In one embodiment, the present invention also relates to carbohydrate binding modules having a sequence identity to amino acids 1 to 124 of SEQ ID NO: 2 of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In one aspect, the carbohydrate binding modules comprise amino acid sequences that differ by up to 10 amino acids, e.g., 1, 2, 3, 4, 5, 6, 7, 8, 9, or 10, from amino acids 1 to 124 of SEQ ID NO: 2.

The carbohydrate binding module preferably comprises or consists of amino acids 1 to 124 of SEQ ID NO: 2 or an allelic variant thereof; or is a fragment thereof having carbohydrate binding activity.

In another embodiment, the present invention also relates to carbohydrate binding modules encoded by polynucleotides that hybridize under very low stringency conditions, low stringency conditions, medium stringency conditions, medium-high stringency conditions, high stringency conditions, or very high stringency conditions (as defined above) with (i) the nucleotides 61 to 480 of SEQ ID NO: 1, (ii) the cDNA sequence thereof, or (iii) the full-length complement of (i) or (ii) (Sambrook et al., 1989, supra).

In another embodiment, the present invention also relates to carbohydrate binding modules encoded by polynucleotides having a sequence identity to nucleotides 61 to 480 of SEQ ID NO: 1 or the cDNA sequence thereof of at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%

In another embodiment, the present invention also relates to carbohydrate binding module variants of amino acids 1 to 124 of SEQ ID NO: 2 comprising a substitution, deletion, and/or insertion at one or more (e.g., several) positions. In one aspect, the number of amino acid substitutions, deletions and/or insertions introduced into the sequence of amino acids 1 to 124 of SEQ ID NO: 2 is up to 10, e.g., 1, 2, 3, 4, 5, 6, 8, 9, or 10.

In one embodiment, the present invention also relates to carbohydrate binding modules having a sequence identity to amino acids 508 to 541 of SEQ ID NO: 2 of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In one aspect, the carbohydrate binding modules comprise amino acid sequences that differ by up to 10 amino acids, e.g., 1, 2, 3, 4, 5, 6, 7, 8, 9, or 10, from amino acids 508 to 541 of SEQ ID NO: 2.

The carbohydrate binding module preferably comprises or consists of amino acids 508 to 541 of SEQ ID NO: 2 or an allelic variant thereof; or is a fragment thereof having carbohydrate binding activity.

In another embodiment, the present invention also relates to carbohydrate binding modules encoded by polynucleotides that hybridize under medium stringency conditions, medium-high stringency conditions, high stringency conditions, or very high stringency conditions (as defined above) with (i) the nucleotides 61 to 480 of SEQ ID NO: 1, (ii) the cDNA sequence thereof, or (iii) the full-length complement of (i) or (ii) (Sambrook et al., 1989, supra).

In another embodiment, the present invention also relates to carbohydrate binding modules encoded by polynucleotides having a sequence identity to nucleotides 1630 to 1731 of SEQ ID NO: 1 or the cDNA sequence thereof of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%.

In another embodiment, the present invention also relates to carbohydrate binding module variants of amino acids 1630 to 1731 of SEQ ID NO: 2 comprising a substitution, deletion, and/or insertion at one or more (e.g., several) positions. In one aspect, the number of amino acid substitutions, deletions and/or insertions introduced into the sequence of amino acids 508 to 541 of SEQ ID NO: 2 is up to 10, e.g., 1, 2, 3, 4, 5, 6, 8, 9, or 10.

In one embodiment, the present invention also relates to carbohydrate binding modules having a sequence identity to amino acids 1 to 130 of SEQ ID NO: 5 of at least 82%, e.g., at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In one aspect, the carbohydrate binding modules comprise amino acid sequences that differ by up to 10 amino acids, e.g., 1, 2, 3, 4, 5, 6, 7, 8, 9, or 10, from amino acids 1 to 130 of SEQ ID NO: 5.

The carbohydrate binding module preferably comprises or consists of amino acids 1 to 130 of SEQ ID NO: 5 or an allelic variant thereof; or is a fragment thereof having carbohydrate binding activity.

In another embodiment, the present invention also relates to carbohydrate binding modules encoded by polynucleotides that hybridize under medium stringency conditions, medium-high stringency conditions, high stringency conditions, or very high stringency conditions (as defined above) with (i) the nucleotides 82 to 586 of SEQ ID NO: 4, (ii) the cDNA sequence thereof, or (iii) the full-length complement of (i) or (ii) (Sambrook et al., 1989, supra).

In another embodiment, the present invention also relates to carbohydrate binding modules encoded by polynucleotides having a sequence identity to nucleotides 82 to 586 of SEQ ID NO: 4 or the cDNA sequence thereof of at least 82%, e.g., at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%.

In another embodiment, the present invention also relates to carbohydrate binding module variants of amino acids 1 to 130 of SEQ ID NO: 5 comprising a substitution, deletion, and/or insertion at one or more (e.g., several) positions. In one aspect, the number of amino acid substitutions, deletions and/or insertions introduced into the sequence of amino acids 1 to 130 of SEQ ID NO: 5 is up to 10, e.g., 1, 2, 3, 4, 5, 6, 8, 9, or 10.

In one embodiment, the present invention also relates to carbohydrate binding modules having a sequence identity to amino acids 492 to 526 of SEQ ID NO: 5 of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%. In one aspect, the carbohydrate binding modules comprise amino acid sequences that differ by up to 10 amino acids, e.g., 1, 2, 3, 4, 5, 6, 7, 8, 9, or 10, from amino acids 492 to 526 of SEQ ID NO: 5. The carbohydrate binding module preferably comprises or consists of amino acids 492 to 526 of SEQ ID NO: 5 or an allelic variant thereof; or is a fragment thereof having carbohydrate binding activity.

In another embodiment, the present invention also relates to carbohydrate binding modules encoded by polynucleotides that hybridize under very low stringency conditions, low stringency conditions, medium stringency conditions, medium-high stringency conditions, high stringency conditions, or very high stringency conditions (as defined above) with (i) the nucleotides 1781 to 1885 of SEQ ID NO: 4, (ii) the cDNA sequence thereof, or (iii) the full-length complement of (i) or (ii) (Sambrook et al., 1989, supra).

In another embodiment, the present invention also relates to carbohydrate binding modules encoded by polynucleotides having a sequence identity to nucleotides 1781 to 1885 of SEQ ID NO: 4 or the cDNA sequence thereof of at least 81%, e.g., at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100%

In another embodiment, the present invention also relates to carbohydrate binding module variants of amino acids 492 to 526 of SEQ ID NO: 5 comprising a substitution, deletion, and/or insertion at one or more (e.g., several) positions. In one aspect, the number of amino acid substitutions, deletions and/or insertions introduced into the sequence of amino acids 492 to 526 of SEQ ID NO: 5 is up to 10, e.g., 1, 2, 3, 4, 5, 6, 8, 9, or 10.

A catalytic domain operably linked to the carbohydrate binding module may be from a hydrolase, isomerase, ligase, lyase, oxidoreductase, or transferase, e.g., an aminopeptidase, amylase, carbohydrase, carboxypeptidase, catalase, cellobiohydrolase, cellulase, chitinase, cutinase, cyclodextrin glycosyltransferase, deoxyribonuclease, endoglucanase, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phytase, polyphenoloxidase, proteolytic enzyme, ribonuclease, transglutaminase, xylanase, or beta-xylosidase. The polynucleotide encoding the catalytic domain may be obtained from any prokaryotic, eukaryotic, or other source.

Polynucleotides

The present invention also relates to polynucleotides encoding a polypeptide, a catalytic domain, or carbohydrate binding module of the present invention, as described herein. In an embodiment, the polynucleotide encoding the polypeptide, catalytic domain, or carbohydrate binding module of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Ascobolus* or a related organism and thus, for example, may be an allelic or species variant of the polypeptide encoding region of the polynucleotide. Alternatively, the polynucleotides may be cloned from a strain of *Chaetomium* or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, SEQ ID NO: 4 or the cDNA sequence thereof, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dana (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (*Endomycetales*), basidiosporogenous yeast, and yeast belonging to the Fungi Imperfecti (*Blastomycetes*). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Ascobolus* cell. In another aspect, the cell is a *Ascobolus stictoideus* cell. In a further aspect, the cell is a *Chaetomium* cell. In another aspect, the cell is a *Chaetomium virescens* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide or domain may be constructed in accordance with methods known in the art. In short, the plant or plant cell is constructed by incorporating one or more expression constructs encoding the polypeptide or domain into the plant host genome or chloroplast genome and propagating the resulting modified plant or plant cell into a transgenic plant or plant cell.

The expression construct is conveniently a nucleic acid construct that comprises a polynucleotide encoding a polypeptide or domain operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide or domain is desired to be expressed. For instance, the expression of the gene encoding a polypeptide or domain may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the chlorella virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide or domain in the plant. For instance, the promoter enhancer element may be an intron that is placed between the promoter and the polynucleotide encoding a polypeptide or domain. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide or domain can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art. The fermentation broth formulations or cell compositions may further comprise multiple enzymatic activities, such as one or more (e.g., several) enzymes selected from the group consisting of a cellulase, a hemicellulase, an esterase, an expansin, a laccase, a ligninolytic enzyme, a pectinase, a peroxidase, a protease, and a swollenin. The fermentation broth formulations or cell compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of uses of the compositions of the present invention. The dosage of the composition and other conditions under which the composition is used may be determined on the basis of methods known in the art.

Uses

The mannanases of the invention may be used in applications where mannan needs to be degraded. Examples of where mannanases could be used are in the production of bioethanol from softwood and palm kernel press cake, for the improvement of animal feed and in the hydrolysis of coffee. Furthermore, guar gum is used in many food products and in the oil and gas industry, so the mannanases of the invention could be used in detergents to remove mannan containing stains, for hydraulic fracturing to create subterranean fractures that extend from the borehole into rock formation in order to increase the rate at which fluids can be produced by the formation or for cleaning borehole filtercake. The mannan may thus be used in fracturing of a subterranean formation perpetrated by a well bore or the mannan may be used as a component in borehole filtercake.

The mannan may be used for degrading a cellulosic material, for producing a fermentation product and for fermenting a cellulosic material e.g., in a process for producing a fermentation product, comprising: (a) saccharifying a cellulosic material with an enzyme composition in the presence of the polypeptide having mannanase activity of the present invention; (b) fermenting the saccharified cellulosic material with one or more fermenting microorganisms to produce the fermentation product; and (c) recovering the fermentation product from the fermentation. The cellulosic material may be pretreated before saccharification.

Certain mannanases of the invention may be used for preventing or removing biofilm on items such as textiles and/or fabric. Such mannanases preferably have least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 3 or the mature polypeptide of SEQ ID NO: 2;

Biofilm can develop on textile when microorganisms are present on an item and stick together on the item. Some microorganisms tend to adhere to the surface of items such as textiles. Some microorganisms adhere to such surfaces and form a biofilm on the surface. The biofilm may be sticky and the adhered microorganisms and/or the biofilm may be difficult to remove. Furthermore the biofilm adhere soil due to the sticky nature of the biofilm. The commercial laundry detergent compositions available on the marked do not remove such adhered microorganisms or biofilm.

The present invention concerns the use of a polypeptide having mannanase activity for preventing, reducing or removing a biofilm from an item, wherein the polypeptide is obtained from a fungal source and wherein the item is a textile. In one embodiment of the invention the polypeptide having mannanase activity is used for preventing, reducing or removing the stickiness of an item.

Enzyme Compositions

The present invention also relates to compositions comprising a polypeptide of the present invention. Preferably, the compositions are enriched in such a polypeptide. The term "enriched" indicates that the cellobiohydrolase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of a cellulase, a hemicellulase, an AA9 polypeptide having cellulolytic enhancing activity, an esterase, an expansin, a laccase, a ligninolytic enzyme, a pectinase, a peroxidase, a protease, and a swollenin. The compositions may also comprise one or more (e.g., several) enzymes selected from the group consisting of a hydrolase, an isomerase, a ligase, a lyase, an oxidoreductase, or a transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

The compositions may be prepared in accordance with methods known in the art and may be in the form of a liquid or a dry composition. The compositions may be stabilized in accordance with methods known in the art.

Examples are given below of uses of the compositions of the present invention. The dosage of the composition and other conditions under which the composition is used may be determined on the basis of methods known in the art.

The Invention is Further Summarized in the Below Paragraphs:

1. A polypeptide having mannanase activity, selected from the group consisting of:
   (a) a polypeptide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 3 or the mature polypeptide of SEQ ID NO: 2;
   (b) a polypeptide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 6 or the mature polypeptide of SEQ ID NO: 5;
   (c) a polypeptide encoded by a polynucleotide that hybridizes under very low, low, medium, medium-high, high, or very high stringency conditions with:
      (i) the mature polypeptide coding sequence of SEQ ID NO: 1,
      (ii) the cDNA sequence thereof, or
      (iii) the full-length complement of (i) or (ii);
   (d) a polypeptide encoded by a polynucleotide that hybridizes under medium, medium-high, high, or very high stringency conditions with:
      (i) the mature polypeptide coding sequence of SEQ ID NO: 4,
      (ii) the cDNA sequence thereof, or
      (iii) the full-length complement of (i) or (ii);
   (e) a polypeptide encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or the cDNA sequence thereof;
   (f) a polypeptide encoded by a polynucleotide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 4 or the cDNA sequence thereof;

(g) a variant of SEQ ID NO: 3 or the mature polypeptide of SEQ ID NO: 2 comprising a substitution, deletion, and/or insertion at one or more (e.g., several) positions;

(h) a variant of SEQ ID NO: 6 or the mature polypeptide of SEQ ID NO: 5 comprising a substitution, deletion, and/or insertion at one or more (e.g., several) positions; and (i) a fragment of the polypeptide of (a), (b), (c), (d), (e), (f), (g) or (h) that has mannanase activity.

2. The polypeptide of paragraph 1, selected from the group consisting of:
   (a) a polypeptide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to SEQ ID NO: 3 or the mature polypeptide of SEQ ID NO: 2; and
   (b) a polypeptide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity SEQ ID NO: 6 or the mature polypeptide of SEQ ID NO: 5.

3. The polypeptide of any of paragraphs 1-2, comprising or consisting of SEQ ID NO: 2, SEQ ID NO: 3, SEQ ID NO: 5, SEQ ID NO: 6 or the mature polypeptide of SEQ ID NO: 2 or SEQ ID NO: 5.

4. The polypeptide of any of paragraphs 1-3, wherein the mature polypeptide corresponds to amino acids 1 to 541 of SEQ ID NO: 2, amino acids 121 to 541 of SEQ ID NO: 2 or amino acids 1 to 526 of SEQ ID NO: 5.

5. A polypeptide comprising a catalytic domain selected from the group consisting of:
   (a) a catalytic domain having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 128 to 446 of SEQ ID NO: 2;
   (b) a catalytic domain having at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 135 to 448 of SEQ ID NO: 5;
   (c) a catalytic domain encoded by a polynucleotide that hybridizes under very low, low, medium, medium-high, high, or very high stringency conditions with:
      (i) nucleotides 490 to 1446 of SEQ ID NO: 1,
      (ii) the cDNA sequence thereof, or
      (iii) the full-length complement of (i) or (ii);
   (d) a catalytic domain encoded by a polynucleotide that hybridizes under medium-high, high, or very high stringency conditions with:
      (i) nucleotides 599 to 1651 of SEQ ID NO: 4,
      (ii) the cDNA sequence thereof, or
      (iii) the full-length complement of (i) or (ii);
   (e) a catalytic domain encoded by a polynucleotide having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 490 to 1446 of SEQ ID NO: 1 or the cDNA sequence thereof;
   (f) a catalytic domain encoded by a polynucleotide having at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 599 to 1651 of SEQ ID NO: 4 or the cDNA sequence thereof;
   (g) a variant of amino acids 128 to 446 of SEQ ID NO: 2 comprising a substitution, deletion, and/or insertion at one or more (e.g., several) positions; and
   (h) a variant of amino acids 135 to 448 of SEQ ID NO: 5 comprising a substitution, deletion, and/or insertion at one or more (e.g., several) positions; and
   (i) a fragment of the catalytic domain of (a), (b), (c), (d), (e), (f), (g) or (h) that has mannanase activity.

6. The polypeptide of paragraph 5, further comprising one or more carbohydrate binding modules.

7. A polypeptide comprising a carbohydrate binding module operably linked to a catalytic domain, wherein the binding module is selected from the group consisting of:
   (a) a carbohydrate binding module having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 1 to 124 of SEQ ID NO: 2;
   (b) a carbohydrate binding module having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 508 to 541 of SEQ ID NO: 2;
   (c) a carbohydrate binding module having at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 1 to 130 of SEQ ID NO: 5;
   (d) a carbohydrate binding module having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to amino acids 492 to 526 of SEQ ID NO: 5;
   (e) a carbohydrate binding module encoded by a polynucleotide that hybridizes under very low, low, medium, medium-high, high, or very high stringency conditions with:
      (i) nucleotides 61 to 480 of SEQ ID NO: 1,
      (ii) the cDNA sequence thereof, or
      (iii) the full-length complement of (i) or (ii);
   (f) a carbohydrate binding module encoded by a polynucleotide that hybridizes under medium, medium-high, high, or very high stringency conditions with:
      (i) nucleotides 1630 to 1731 of SEQ ID NO: 1,
      (ii) the cDNA sequence thereof, or
      (iii) the full-length complement of (i) or (ii);

(g) a carbohydrate binding module encoded by a polynucleotide that hybridizes under medium, medium-high, high, or very high stringency conditions with:
(i) nucleotides 82 to 586 of SEQ ID NO: 4,
(ii) the cDNA sequence thereof, or
(iii) the full-length complement of (i) or (ii);
(h) a carbohydrate binding module encoded by a polynucleotide that hybridizes under medium, medium-high, high, or very high stringency conditions with:
(i) nucleotides 1781 to 1885 of SEQ ID NO: 4,
(ii) the cDNA sequence thereof, or
(iii) the full-length complement of (i) or (ii);
(i) a carbohydrate binding module encoded by a polynucleotide having at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 61 to 480 of SEQ ID NO: 1 or the cDNA sequence thereof;
(j) a carbohydrate binding module encoded by a polynucleotide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 1630 to 1731 of SEQ ID NO: 1 or the cDNA sequence thereof;
(k) a carbohydrate binding module encoded by a polynucleotide having at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 82 to 586 of SEQ ID NO: 4 or the cDNA sequence thereof;
(l) a carbohydrate binding module encoded by a polynucleotide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to nucleotides 1781 to 1885 of SEQ ID NO: 4 or the cDNA sequence thereof;
(m) a variant of amino acids 1 to 124 of SEQ ID NO: 2 comprising a substitution, deletion, and/or insertion at one or more (e.g., several) positions; and
(n) a variant of amino acids 508 to 541 of SEQ ID NO: 2 comprising a substitution, deletion, and/or insertion at one or more (e.g., several) positions; and
(o) a variant of amino acids 1 to 130 of SEQ ID NO: 5 comprising a substitution, deletion, and/or insertion at one or more (e.g., several) positions; and
(p) a variant of amino acids 492 to 526 of SEQ ID NO: 5 comprising a substitution, deletion, and/or insertion at one or more (e.g., several) positions; and
(q) a fragment of the carbohydrate binding module of (a), (b), (c), (d), (e), (f), (g), (h), (i), (j), (k), (l), (m), (n), (o) or (p) that has carbohydrate binding activity.

8. A composition comprising the polypeptide of any of paragraphs 1-7.

9. The composition of paragraph 8, further comprising one or more additional enzymes.

10. The composition of any of paragraphs 8-9, further comprising one or more detergent components.

11. The composition of any of paragraphs 8-9, further comprising at least one fat soluble vitamin and/or at least one water soluble vitamin and/or at least one trace mineral.

12. Use of a composition according to any of paragraphs 8-10 for degrading mannan, such as linear mannan, galactomannan, glucomannan and galactoglucomannan.

13. The use of paragraph 12 for controlling the viscosity of drilling fluids.

14. The use of paragraph 12 for washing or cleaning a textile and/or a hard surface such as dish wash.

15. The use of the composition of paragraph 10 for laundering and/or hard surface cleaning, wherein the composition has an enzyme detergency benefit.

16. A method for degrading mannan, such as linear mannan, galactomannan, glucomannan and galactoglucomannan, comprising applying a composition comprising any of paragraphs 1-7 to the mannan.

17. The method of paragraph 16, wherein the mannan is on the surface of a textile or hard surface, such as dish wash.

18. The method of paragraph 16, wherein the mannan is used in fracturing of a subterranean formation perpetrated by a well bore.

19. The method of paragraph 18, wherein the mannan is a component in borehole filtercake.

20. A method for producing a coffee extract, comprising the steps:
(a) providing roast and ground coffee beans;
(b) adding to said coffee beans water and a polypeptide of any of paragraphs 1-7;
(c) incubating to make an aqueous coffee extract; and
(d) separating the coffee extract from the extracted coffee beans.

21. The method of paragraph 20, wherein step (b) further comprises addition of an enzyme having β-1,3-galactanase activity.

22. A process for degrading a cellulosic material, comprising: treating the cellulosic material with an enzyme composition in the presence of the polypeptide having mannanase activity of any of paragraphs 1-7.

23. A process for producing a fermentation product, comprising:
(a) saccharifying a cellulosic material with an enzyme composition in the presence of the polypeptide having mannanase activity of any of paragraphs 1-7;
(b) fermenting the saccharified cellulosic material with one or more fermenting microorganisms to produce the fermentation product; and
(c) recovering the fermentation product from the fermentation.

24. The process of any of paragraphs 22-23, wherein the cellulosic material is pretreated.

25. The process of any of paragraphs 22-24, wherein the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

26. A process of fermenting a cellulosic material, comprising: fermenting the cellulosic material with one or more fermenting microorganisms, wherein the cellulosic material is saccharified with an enzyme composition in the presence of the polypeptide having mannanase activity of any of paragraphs 1-7.

27. The process of paragraph 26, wherein the cellulosic material is pretreated before saccharification.

28. The process of any of paragraphs 26-27, wherein the enzyme composition comprises one or more enzymes selected from the group consisting of cellulase, AA9 polypeptide, hemicellulase, esterase, expansin, ligninolytic enzyme, oxidoreductase, pectinase, protease, and swollenin.
29. A polynucleotide encoding the polypeptide of any of paragraphs 1-7.
30. A nucleic acid construct or expression vector comprising the polynucleotide of paragraph 29 operably linked to one or more control sequences that direct the production of the polypeptide in an expression host.
31. A recombinant host cell comprising the polynucleotide of paragraph 29 operably linked to one or more control sequences that direct the production of the polypeptide.
32. A method of producing the polypeptide of any of paragraphs 1-7, comprising:
    (a) cultivating a cell, which in its wild-type form produces the polypeptide, under conditions conductive for production of the polypeptide; and
    (b) recovering the polypeptide.
33. A method of producing the polypeptide of any of paragraphs 1-7, comprising:
    (a) cultivating a host cell of paragraph 31 under conditions conducive for production of the polypeptide; and
    (b) recovering the polypeptide.
34. A transgenic plant, plant part or plant cell transformed with a polynucleotide encoding the polypeptide of any of paragraphs 1-7.
35. A method of producing the polypeptide of any of paragraphs 1-7, comprising:
    (a) cultivating a transgenic plant or a plant cell of paragraph 34 under conditions conducive for production of the polypeptide; and
    (b) recovering the polypeptide.
36. A whole broth formulation or cell culture composition comprising a polypeptide of any of paragraphs 1-7.
37. Use of the polypeptide according to paragraph 1 for preventing, reducing or removing a biofilm from an item.
38. Use according to paragraph 37, wherein malodor is reduced or removed from the item.

The present invention is further described by the following examples that should not be construed as limiting the scope of the invention.

EXAMPLES

Strains

*Chaetomium virescens* CBS547.75 was used as the source of a polypeptide having mannanase activity. The strain was isolated from wheat straw compost, prepared for mushroom growing in 1974 in Ludhiana, Punjab.

*Ascobolus stictoideus* QA026 was used as the source of a polypeptide having mannanase activity. The strain was isolated in Denmark on or before 1991 in collaboration with Institut for Sporeplanter (Ifs), University of Copenhagen, Denmark.

*Aspergillus oryzae* MT3568 strain was used for expression of the *Chaetomium virescens* and *Ascobolus stictoideus* genes encoding the polypeptide having mannanase activity. A. oryzae MT3568 is an amdS (acetamidase) disrupted gene derivative of *Aspergillus oryzae* JaL355 (WO 2002/40694) in which pyrG auxotrophy was restored by disrupting the *A. oryzae* acetamidase (amdS) gene.

Materials

Chemicals used as buffers and substrates were commercial products of at least reagent grade.

Media and Solutions

YP+2% glucose medium was composed of 1% yeast extract, 2% peptone and 2% glucose.

PDA agar plates were composed of potato infusion (potato infusion was made by boiling 300 g of sliced (washed but unpeeled) potatoes in water for 30 minutes and then decanting or straining the broth through cheesecloth. Distilled water was then added until the total volume of the suspension was one liter, followed by 20 g of dextrose and 20 g of agar powder. The medium was sterilized by autoclaving at 15 psi for 15 minutes (Bacteriological Analytical Manual, 8th Edition, Revision A, 1998).

LB plates were composed of 10 g of Bacto-Tryptone, 5 g of yeast extract, 10 g of sodium chloride, 15 g of Bacto-agar, and deionized water to 1 liter. The medium was sterilized by autoclaving at 15 psi for 15 minutes (Bacteriological Analytical Manual, 8th Edition, Revision A, 1998).

COVE sucrose plates were composed of 342 g Sucrose (Sigma S-9378), 20 g Agar powder, 20 ml Cove salt solution (26 g $MgSO_4.7H_2O$, 26 g KCL, 26 g $KH_2PO_4$, 50 ml Cove trace metal solution) and deionized water to 1 liter), and deionized water to 1 liter). The medium was sterilized by autoclaving at 15 psi for 15 minutes (Bacteriological Analytical Manual, 8th Edition, Revision A, 1998). The medium was cooled to 60° C. and added 10 mM acetamide, 15 mM CsCl, Triton X-100 (50 µl/500 ml)).

Cove trace metal solution was composed of 0.04 g $Na_2B_4O_7.10H_2O$, 0.4 g $CuSO_4.5H_2O$, 1.2 g $FeSO_4.7H_2O$, 0.7 g $MnSO_4.H_2O$, 0.8 g $Na_2MoO_4.2H_2O$, 10 g $ZnSO_4.7H_2O$, and deionized water to 1 liter.

Reducing End Assay

For estimating the mannose yield after substrate hydrolysis, a reducing end assay developed by Lever (1972), Anal. Biochem. 47: 273-279, was used. The assay is based on 4-hydroxybenzoic acid hydrazide, which under alkaline conditions reacts with the reducing ends of saccharides. The product is a strong yellow anion, which absorbs at 410 nm.

Method

4-Hydroxybenzhydrazide (PAHBAH) (Sigma, H9882) was diluted in PAHBAH buffer to a concentration of 15 mg/ml. PAHBAH buffer contained: 50 g/L K-Na-tartrate (Merck, 1.08087) and 20 g/L sodium hydroxide (Sigma, S8045). This PAHBAH mix was made just before usage.

70 µl PAHBAH mix and MiliQ water were mixed in a 96 well PCR plate (Thermo Scientific). Samples from hydrolysis experiment were added. Samples and MiliQ always reached the total volume of 150 µl, but the dilution of the sample differed. The plate was sealed with Adhesive PCR Sealing Foil Sheets (Thermo Scientific). Plates were incubated at 95° C. for 10 min, cooled down and kept at 10° C. for 1 min in PTC-200 Thermal Cycler (MJ Research). 100 µl sample was transferred to a 96 well microtiter plate, flat bottomed (Nunc™) and color development measured at 405 nm on a SpectraMax 190 Absorbance Microplate Reader (Molecular Devices). Results were compared to mannose standards, that had undergone the same treatment and dilution as the samples to which they were compared.

Malodor Assay

Analysis of E-2-nonenal on textile using an electronic nose.

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyze 5 mL headspace from the capped vials in a Heracles II Electronic nose from Alpha M.O.S., France (double column gas chromatograph with 2 FIDs, column 1: MXT5 and column 2: MXT1701) after 20 minutes incubation at 40° C.

N-Terminal Sequencing

N-terminal sequencing analyses were performed using an Applied Biosystems Procise® protein sequencing system. The samples were purified on a Novex® precast 4-20% SDS polyacrylamide gel (Life Technologies). The gel was run according to manufacturer's instructions and blotted to a ProBlott® PVDF membrane (Applied Biosystems). For N-terminal amino acid sequencing the main protein band was cut out and placed in the blotting cartridge of the Procise® protein sequencing system. The N-terminal sequencing was carried out using the method run file for PVDF membrane samples (Pulsed liquid PVDF) according to manufacturer's instructions. The N-terminal amino acid sequence can be deduced from the 7 chromatograms corresponding to amino acid residues 1 to 7 by comparing the retention time of the peaks in the chromatograms to the retention times of the PTH-amino-acids in the standard chromatogram.

Mass Spectrometry (MS/MS) Sequencing

Protein identification was performed by tandem mass spectrometry (MS/MS) analysis of tryptic peptides from an in gel digest. First the sample was reduced by DTT and alkylated with Iodacetamide. The reduced and alkylated sample was then applied to SDS-gel electrophoresis.

The gel was run and stained according to manufacturer's instructions (Novex® precast 4-20% SDS polyacrylamide gel (Life Technologies). The main protein band was cut out and the gel piece digested over night by Sequencing Grade trypsin (Roche). Following digestion the generated tryptic peptides were extracted and analysed on an Orbitrap LTQ XL mass spectrometer (Thermo Scientific) where peptide masses and peptide fragment masses are measured. For protein identification the experimentally obtained masses were compared with the theoretical peptide masses and peptide fragment masses of proteins stored in databases by the mass search program Mascot (*Matrix* science).

Example 1: Source of DNA Sequence Information for *Ascobolus stictoideus* Strain QA026

Genomic sequence information was generated by Illumina DNA sequencing at Fasteris genome sequencing facility at Plan-les-Ouates, Switcherland from genomic DNA isolated from *Ascobolus stictoideus* Strain QA026 (Department of Plant and Environmental Sciences, University of Copenhagen, Denmark). A preliminary assembly of the genome was analyzed using the IDBA Iterative de Bruijn Graph De Novo Sequence Assembler v0.2 (Y Peng, H C M Leung, S M Yiu, F Y L Chin 2010, Research in Computational Molecular Biology 6044, pp 426-440). Gene models constructed by the software were used as a starting point for detecting GH26 homologues in the genome. More precise gene models were constructed manually using multiple known GH26 protein sequences as a guide.

Example 2: *Ascobolus stictoideus* Strain QA026 Genomic DNA Extraction

To generate genomic DNA for PCR amplification, *Ascobolus stictoideus* Strain QA026 was propagated on PDA agar plates by growing at 26° C. for 7 days. Spores harvested from the PDA plates were used to inoculate 100 ml of MEX-1 medium (medium B in WO 98/38288) in a baffled shake flask and incubated at 26° C. for 48 hours with agitation at 85 rpm.

Genomic DNA was isolated according to a modified DNeasy Plant Maxi kit protocol (Qiagen Danmark, Copenhagen, Denmark). The fungal material from the above culture was harvested by centrifugation at 14,000×g for 2 minutes. The supernatant was removed and the 0.5 g of the pellet was frozen in liquid nitrogen with quartz sand and grinded to a fine powder in a pre-chilled mortar. The powder was transferred to a 15 ml centrifuge tube and added 5 ml buffer AP1 (preheated to 65° C.) and 10 µl RNase A stock solution (100 mg/ml) followed by vigorous vortexing. After incubation for 10 minutes at 65° C. with regular inverting of the tube, 1.8 ml buffer AP2 was added to the lysate by gentle mixing followed by incubation on ice for 10 min. The lysate was then centrifugated at 3000×g for 5 minutes at room temperature and the supernatant was decanted into a QIAshredder maxi spin column placed in a 50 ml collection tube. This was followed by centrifugation at 3000×g for 5 minutes at room temperature. The flow-through was transferred into a new 50 ml tube and added 1.5 volumes of buffer AP3/E followed by vortexing. 15 ml of the sample was transferred into a DNeasy Maxi spin column placed in a 50 ml collection tube and centrifuged at 3000×g for 5 minutes at room temperature. The flow-through was discarded and 12 ml buffer AW was added to the DNeasy Maxi spin column placed in a 50 ml collection tube and centrifuged at 3000×g for 10 minutes at room temperature. After discarding the flow-through, centrifugation was repeated to dispose of the remaining alcohol. The DNeasy Maxi spin column was transferred to a new 50 ml tube and 0.5 ml buffer AE (preheated to 70° C.) was added. After incubation for 5 minutes at room temperature, the sample was eluded by centrifugation at 3000×g for 5 minutes at room temperature. Elution was repeated with an additional 0.5 ml buffer AE and the eluates were combined. The concentration of the harvested DNA was measured by a UV spectrophotometer at 260 nm.

Example 3: Construction of an *Aspergillus oryzae* Expression Vector Containing *Ascobolus stictoideus* Strain QA026 Genomic Sequence Encoding a Family GH26 Polypeptide Having Mannanase Activity Two synthetic oligonucleotide primers shown below were designed to PCR amplify the *Ascobolus stictoideus* Strain QA026 P335AW gene (SEQ ID NO: 1) from the genomic DNA prepared in Example 2. An IN-FUSION™ Cloning Kit (BD Biosciences, Palo Alto, Calif., USA) was used to clone the fragment directly into the expression vector pDau109 (WO 2005/042735).

F-P335AW

5'-acacaactggggatccaccATGCGTTTCTCTCTCT-GCGTCGG-3' (SEQ ID NO: 7)

R-P335AW

5'-ccctctagatctcgagCCTTCCTCCTTTCCTAGCAGCT-3' (SEQ ID NO: 8)

Capital letters represent gene sequence. The underlined sequence is homologous to the insertion sites of pDau109.

An MJ Research PTC-200 DNA engine was used to perform the PCR reaction. A Phusion® High-Fidelity PCR Kit (Finnzymes Oy, Espoo, Finland) was used for the PCR amplification. The PCR reaction was composed of 5 µl of 5×HF buffer (Finnzymes Oy, Espoo, Finland), 0.5 µl of dNTPs (10 mM), 0.5 µl of Phusion® DNA polymerase (0.2 units/µl) (Finnzymes Oy, Espoo, Finland), 2 µl of primer F-P335AW (2.5 µM), 2 µl of primer R-P335AW (2.5 µM), 0.5 µl of *Ascobolus stictoideus* genomic DNA (100 ng/µl), and 14.5 µl of deionized water in a total volume of 25 µl. The PCR conditions were 1 cycle at 95° C. for 2 minutes. 35 cycles each at 98° C. for 10 seconds, 60° C. for 30 seconds, and 72° C. for 2.5 minutes; and 1 cycle at 72° C. for 10 minutes. The sample was then held at 12° C. until removed from the PCR machine.

The reaction products were isolated by 1.0% agarose gel electrophoresis using 40 mM Tris base, 20 mM sodium acetate, 1 mM disodium EDTA (TAE) buffer where a 1803 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Bam HI and Xho I digested pDau109 using an IN-FUSION™ Cloning Kit resulting in plasmid pP335AW. Cloning of the P335AW gene into Bam HI-Xho I digested pDau109 resulted in the transcription of the *Ascobolus stictoideus* P335AW gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P335AW GH26 construct. The treated plasmid and insert were transformed into One Shot® TOP10F' Chemically Competent *E. coli* cells (Invitrogen, Carlsbad, Calif., USA) according to the manufacturer's protocol and plated onto LB plates supplemented with 0.1 mg of ampicillin per ml. After incubating at 37° C. overnight, colonies were seen growing under selection on the LB ampicillin plates. Four colonies transformed with the P335AW GH26 construct were cultivated in LB medium supplemented with 0.1 mg of ampicillin per ml and plasmid was isolated with a QIAprep Spin Miniprep Kit (QIAGEN Inc., Valencia, Calif., USA) according to the manufacturer's protocol.

Isolated plasmids were sequenced with vector primers and P335AW gene specific primers in order to determine a representative plasmid expression clone that was free of PCR errors.

Example 4: Characterization of the *Ascobolus stictoideus* QA026 Genomic Sequence Encoding a P335AW GH26 Polypeptide Having Mannanase Activity DNA sequencing of the *Ascobolus stictoideus* QA026 P335AW GH26 genomic clone was performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

Example 5: Expression of the *Ascobolus stictoideus* GH26 Mannanase P335AW

The expression plasmid pP335AW was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Ascobolus stictoideus* GH26 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, Calif., USA) by Coomassie staining. One transformant was selected for further work and designated *Aspergillus oryzae* 17.4.

For larger scale production, *Aspergillus oryzae* 17.4 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 µm PES filter (Thermo Fisher Scientific, Roskilde, Denmark). Fresh culture broth from this transformant produced a single band of GH26 protein of approximately 67 kDa. The identity of the band as the *Ascobolus stictoideus* GH26 polypeptide was verified by peptide sequencing. The difference between apparent and observed size of the recombinant proteins can likely be attributed to glycosylation and/or other posttranslational modifications.

Example 6: Alternative Method for Producing the *Ascobolus stictoideus* GH26 Mannanase P335AW Based on the nucleotide sequence identified as SEQ ID NO: 1, a synthetic gene can be obtained from a number of vendors such as Gene Art (GENEART AG BioPark, Josef-Engert-Str. 11, 93053, Regensburg, Germany) or DNA 2.0 (DNA2.0, 1430 O'Brien Drive, Suite E, Menlo Park, Calif. 94025, USA). The synthetic gene can be designed to incorporate additional DNA sequences such as restriction sites or homologous recombination regions to facilitate cloning into an expression vector.

Using the two synthetic oligonucleotide primers F-P335AW and F-P335AW described above, a simple PCR reaction can be used to amplify the full-length open reading frame from the synthetic gene of SEQ ID NO: 1. The gene can then be cloned into an expression vector for example as described above and expressed in a host cell, for example in *Aspergillus oryzae* as described above.

Example 7: Source of DNA Sequence Information for *Chaetomium virescens* Strain CBS547.75

Genomic sequence information was generated by Illumina DNA sequencing at The National Center for Genome Resources in Santa Fe, N. Mex. from genomic DNA isolated from *Chaetomium virescens* Strain CBS547.75. A preliminary assembly of the genome was analyzed using the Abyss 1.2.0 Sequence Assembler (GSC Software Center, Vancouver, Canada). Gene models constructed by the software were used as a starting point for detecting GH26 homologues in the genome. More precise gene models were constructed manually using multiple known GH26 protein sequences as a guide.

Example 8: *Chaetomium virescens* Strain CBS547.75 Genomic DNA Extraction

To generate genomic DNA for PCR amplification, *Chaetomium virescens* Strain CBS547.75 was propagated on PDA agar plates by growing at 26° C. for 7 days. Spores harvested from the PDA plates were used to inoculate 25 ml of YP+2% glucose medium in a baffled shake flask and incubated at 26° C. for 72 hours with agitation at 85 rpm.

Genomic DNA was isolated according to a modified DNeasy Plant Maxi kit protocol (Qiagen Danmark, Copenhagen, Denmark). The fungal material from the above culture was harvested by centrifugation at 14,000×g for 2 minutes. The supernatant was removed and the 0.5 g of the pellet was frozen in liquid nitrogen with quartz sand and grinded to a fine powder in a pre-chilled mortar. The powder was transferred to a 15 ml centrifuge tube and added 5 ml buffer AP1 (preheated to 65° C.) and 10 µl RNase A stock solution (100 mg/ml) followed by vigorous vortexing. After incubation for 10 minutes at 65° C. with regular inverting of the tube, 1.8 ml buffer AP2 was added to the lysate by gentle mixing followed by incubation on ice for 10 min. The lysate was then centrifugated at 3000×g for 5 minutes at room temperature and the supernatant was decanted into a QIAshredder maxi spin column placed in a 50 ml collection tube. This was followed by centrifugation at 3000×g for 5 minutes at room temperature. The flow-through was transferred into a new 50 ml tube and added 1.5 volumes of buffer AP3/E followed by vortexing. 15 ml of the sample was transferred into a DNeasy Maxi spin column placed in a 50 ml collection tube and centrifuged at 3000×g for 5 minutes at room temperature. The flow-through was discarded and 12 ml buffer AW was added to the DNeasy Maxi spin column placed in a 50 ml collection tube and centrifuged at 3000×g for 10 minutes at room temperature. After discarding the flow-through, centrifugation was repeated to dispose of the remaining alcohol. The DNeasy Maxi spin column was transferred to a new 50 ml tube and 0.5 ml buffer AE (preheated to 70° C.) was added. After incubation for 5 minutes at room temperature, the sample was eluted by centrifugation at 3000×g for 5 minutes at room temperature. Elution was repeated with an additional 0.5 ml buffer AE and the eluates were combined. The concentration of the harvested DNA was measured by a UV spectrophotometer at 260 nm.

Example 9: Construction of an *Aspergillus oryzae* Expression Vector Containing *Chaetomium virescens* Strain CBS547.75 Genomic Sequence Encoding a Family GH26 Polypeptide Having Mannanase Activity Two synthetic oligonucleotide primers shown below were designed to PCR amplify the *Chaetomium virescens* Strain CBS547.75 P335AV gene (SEQ ID NO: 4) from the genomic DNA prepared in Example 2. An IN-FUSION™ Cloning Kit (BD Biosciences, Palo Alto, Calif., USA) was used to clone the fragment directly into the expression vector pDau109 (WO 2005/042735).

F-P335AV
(SEQ ID NO: 9)
5'-acacaactggggatccaccATGGACAAAATCCTCAGATACTTTCTC T-3'

R-P335AV
(SEQ ID NO: 10)
5'-ccctctagatctcgagCATGCTTTAACCGCCTGCAA-3'

Capital letters represent gene sequence. The underlined sequence is homologous to the insertion sites of pDau109.

An MJ Research PTC-200 DNA engine was used to perform the PCR reaction. A Phusion® High-Fidelity PCR Kit (Finnzymes Oy, Espoo, Finland) was used for the PCR amplification. The PCR reaction was composed of 5 µl of 5×HF buffer (Finnzymes Oy, Espoo, Finland), 0.5 µl of dNTPs (10 mM), 0.5 µl of Phusion® DNA polymerase (0.2 units/µl) (Finnzymes Oy, Espoo, Finland), 2 µl of primer F-P335AV (2.5 µM), 2 µl of primer R-P335AV (2.5 µM), 0.5 µl of *Chaetomium virescens* genomic DNA (100 ng/µl), and 14.5 µl of deionized water in a total volume of 25 µl. The PCR conditions were 1 cycle at 95° C. for 2 minutes. 35 cycles each at 98° C. for 10 seconds, 60° C. for 30 seconds, and 72° C. for 2.5 minutes; and 1 cycle at 72° C. for 10 minutes. The sample was then held at 12° C. until removed from the PCR machine.

The reaction products were isolated by 1.0% agarose gel electrophoresis using 40 mM Tris base, 20 mM sodium acetate, 1 mM disodium EDTA (TAE) buffer where a 1946 bp product band was excised from the gel and purified using an illustra GFX® PCR DNA and Gel Band Purification Kit (GE Healthcare Life Sciences, Brondby, Denmark) according to the manufacturer's instructions. The fragment was then cloned into Bam HI and Xho I digested pDau109 using an IN-FUSION™ Cloning Kit resulting in plasmid pP335AV. Cloning of the P335AV gene into Bam HI-Xho I digested pDau109 resulted in the transcription of the *Chaetomium virescens* P335AV gene under the control of a NA2-tpi double promoter. NA2-tpi is a modified promoter from the gene encoding the *Aspergillus niger* neutral alpha-amylase in which the untranslated leader has been replaced by an untranslated leader from the gene encoding the *Aspergillus nidulans* triose phosphate isomerase.

The cloning protocol was performed according to the IN-FUSION™ Cloning Kit instructions generating a P335AV GH26 construct. The treated plasmid and insert were transformed into One Shot® TOP10F" Chemically Competent *E. coli* cells (Invitrogen, Carlsbad, Calif., USA) according to the manufacturer's protocol and plated onto LB plates supplemented with 0.1 mg of ampicillin per ml. After incubating at 37° C. overnight, colonies were seen growing under selection on the LB ampicillin plates. Four colonies transformed with the P335AV GH26 construct were cultivated in LB medium supplemented with 0.1 mg of ampicillin per ml and plasmid was isolated with a QIAprep Spin Miniprep Kit (QIAGEN Inc., Valencia, Calif., USA) according to the manufacturer's protocol.

Isolated plasmids were sequenced with vector primers and P335AV gene specific primers in order to determine a representative plasmid expression clone that was free of PCR errors.

Example 10: Characterization of the *Chaetomium virescens* CBS547.75 Genomic Sequence Encoding a P335AV GH26 Polypeptide Having Mannanase Activity DNA sequencing of the *Chaetomium virescens* CBS547.75 P335AV GH26 genomic clone was performed with an Applied Biosystems Model 3700 Automated DNA Sequencer using version 3.1 BIG-DYE™ terminator chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

Example 11: Expression of the *Chaetomium virescens* GH26 Mannanase P335AV

The expression plasmid pP335AV was transformed into *Aspergillus oryzae* MT3568. *Aspergillus oryzae* MT3568 is an AMDS (acetamidase) disrupted derivative of JaL355 (WO 02/40694) in which pyrG auxotrophy was restored in the process of knocking out the *Aspergillus oryzae* acetamidase (AMDS) gene. MT3568 protoplasts are prepared according to the method of European Patent No. 0238023, pages 14-15, which are incorporated herein by reference.

Transformants were purified on COVE sucrose selection plates through single conidia prior to sporulating them on PDA plates. Production of the *Chaetomium virescens* GH26 polypeptide by the transformants was analyzed from culture supernatants of 1 ml 96 deep well stationary cultivations at 30° C. in YP+2% glucose medium. Expression was verified on an E-Page 8% SDS-PAGE 48 well gel (Invitrogen, Carlsbad, Calif., USA) by Coomassie staining. One transformant was selected for further work and designated *Aspergillus oryzae* 16.1.

For larger scale production, *Aspergillus oryzae* 16.1 spores were spread onto a PDA plate and incubated for five days at 37° C. The confluent spore plate was washed twice with 5 ml of 0.01% TWEEN® 20 to maximize the number of spores collected. The spore suspension was then used to inoculate fifteen 500 ml flasks containing 150 ml of Dap-4C medium (WO 2012/103350). The culture was incubated at 30° C. with constant shaking at 100 rpm. At day four post-inoculation, the culture broth was collected by filtration through a bottle top MF75 Supor MachV 0.2 μm PES filter (Thermo Fisher Scientific, Roskilde, Denmark). Fresh culture broth from this transformant produced a single band of GH26 protein of approximately 67 kDa. The identity of the band as the *Chaetomium virescens* GH26 polypeptide was verified by peptide sequencing. The difference between apparent and observed size of the recombinant proteins can likely be attributed to glycosylation and/or other posttranslational modifications.

Example 12: Alternative Method for Producing the *Chaetomium virescens* GH26 Mannanase P335AV Based on the nucleotide sequence identified as SEQ ID NO: 4, a synthetic gene can be obtained from a number of vendors such as Gene Art (GENEART AG BioPark, Josef-Engert-Str. 11, 93053, Regensburg, Germany) or DNA 2.0 (DNA2.0, 1430 O'Brien Drive, Suite E, Menlo Park, Calif. 94025, USA). The synthetic gene can be designed to incorporate additional DNA sequences such as restriction sites or homologous recombination regions to facilitate cloning into an expression vector.

Using the two synthetic oligonucleotide primers F-P335AV and F-P335AV described above, a simple PCR reaction can be used to amplify the full-length open reading frame from the synthetic gene of SEQ ID NO: 4. The gene can then be cloned into an expression vector for example as described above and expressed in a host cell, for example in *Aspergillus oryzae* as described above.

Example 13: Purification of GH26 Mannanases From *Ascobolus stictoideus* (Mature Polypeptide of SEQ ID NO: 2) and *Chaetomium virescens* (Mature Polypeptide of SEQ ID NO: 5)

Filtrated broth was adjusted to pH7.5 and filtrated on 0.22 μm PES filter (Nalge Nunc International, Nalgene labware cat#595-4520). The filtrate was loaded onto a Sephadex™ G-25 (medium) (GE Healthcare, Piscataway, N.J., USA) column equilibrated in 25 mM HEPES pH 7.5. Fractions were collected and analyzed by SDS-PAGE and with spectrophotometric analysis. Elution was performed with 0.7 CVs of elution buffer, which was the same buffer as the equilibration buffer (25 mM Hepes pH 7.5). The eluent was collected in 10 ml fractions. Fractions containing relevant protein were pooled.

The final enzyme concentrations were 0.58 mg/mL for the GH26 mannanases from *Ascobolus stictoideus* (mature polypeptide of SEQ ID NO: 2) and 0.75 mg/mL for the GH26 mannanases from *Chaetomium virescens* (mature polypeptide of SEQ ID NO: 5).

General Description of SDS-PAGE Method 4-12% Nupage® Bis-Tris gel (Life Technologies), run in Nupage® MES SDS Running Buffer (20×) (Life Technologies). Loading buffer was prepared as a 9:1 mix of Novex® Tris-Glycine SDS Sample Buffer (2×) (Life Technologies) and Nupage® Sample Reducing Agent (10×) (Life Technologies). Sample and loading buffer were mixed 1:1 and heated at 95° C. for 5 min at 750 RPM in a Thermomixer Comfort (Eppendorf). Afterwards samples were quickly spun down. The loaded amount of sample mix depended on the size of the wells and the protein concentrations in the samples. 10 μl LMW protein ladder (GE Healthcare) was used as marker. Gels were run at 250 V for 28 min with a maximum of 125 mA and 40 W. Protein bands were visualized by staining with Instant Blue™ (Expedeon).

General Description of Spectrophotometric Analysis

Protein concentrations of purified samples were estimated spectrophotometrically at 280 nm on an 8453-UV-Vis Spectrophotometer (Aglient Technologies), using 1 ml cuvettes with 1 cm light path, and the molar extinction coefficient of the given protein. The molar extinction coefficients of all proteins were estimated by GPMAW 9.20 (Lighthouse Data), and were based on mature proteins without modifications such as glycosylation. To avoid background interference the reference solution was measured as a blank sample on the spectrophotometer. All measurements were made at least in triplicates.

Example 14: Mannanase Activity as Determined by Reducing Ends

The purified mannanases were tested on three different substrates (all from Megazyme): carob galactomannan (Gal:Man, 1:3.5) (5 mg/ml), konjac glucomannan (Glc:Man, 1:1.5) (2.5 mg/ml) and guar gum galactomannan (Gal:Man, 1:1.6) (2.5 mg/ml). In the used konjac glucomannan there were 2.7 acetate groups per 100 sugar units (both glucose and mannose)

Standard and Buffer

Mannose (Sigma, M2069), was dissolved in MiliQ water for preparations of mannose standards. Enzyme and substrate dilution buffer: 50 mM acetic acid (Sigma, 33209)+ 0.01% trition x-100 (Sigma, X100), pH 5. The pH was set with sodium hydroxide (Sigma, S8045).

Preparation of Substrate Solution

The substrate was accurately weighed out in an appropriate beaker and wetted with 96% ethanol (Kemetyl). A magnetic stirrer bare was added and subsequently dilution buffer to approximately 4/5 of the end volume. The beaker was placed immediately on a magnetic stirrer hotplate and the solution was stirred and heated until boiling. The beaker was loosely covered with aluminium foil. When boiling, the beaker was transferred immediately to an ice bath to cool down. The solution was trans-ferred to a volumetric flask and volume adjusted to the end volume with dilution buffer. The solution was mixed with a magnetic stirrer for approximately 5 min.

Enzymes

The GH26 mannanases of the invention along with a known GH5 beta-mannanase from *Trichoderma reesei* (mature polypeptide of SEQ ID NO: 11, concentration 0.66 mg/mL) were tested.

The mannanases were serially diluted in dilution buffer with a factor 3 in 7 steps, giving samples that were diluted the following times: 3, 9, 27, 81, 243, 729 and 2187. All 7 dilutions were tested for each mannanase. To determine the initial rates, the concentrations in the linear range at the very beginning of the curve path, but which were above the limit of quantification were chosen.

Enzymatic Hydrolysis

The hydrolysis volume was 200 µl, 180 µl substrate solution and 20 µl diluted enzyme (purified as described in example 13), and was carried out in 96 well flat bottomed microtiter plates (Nunc™). For negative control, wells without enzyme (blanks) were loaded with 20 µl dilution buffer. Wells without substrate were used to measure the enzymes self-absorption and contained 180 µl dilution buffer instead of substrate. Each plate contained at least one range of mannose standards loaded as 20 µl mannose standard and 180 µl dilution buffer. Plates were sealed with Adhesive PCR Sealing Foil Sheets (Thermo Scientific) and incubated at 37° C. and 950 RPM in a Thermomixer Comfort (Eppendorf). Hydrolysis was carried out for 15 min and stopped immediately when samples were transferred to the alkaline condition in the Reducing End Assay (described herein). Mannose yields were estimated by the reducing end assay.

TABLE 1

Initial hydrolysis rates of GH5 and GH26 mannanases on 3 types of mannose

| Sample name | Initial hydrolysis rate ((µmol/min)/mg EP) | | |
|---|---|---|---|
| | Carob | Konjac | Guar Gum |
| GH26 mannanase from *Chaetomium virescens* (mature polypeptide of SEQ ID NO: 2) | 151 ± 1 | 134 ± 1 | 82 ± 10 |
| GH26 mannanase from *Ascobolus stictoideus* (mature polypeptide of SEQ ID NO: 5) | 389 ± 29 | 228 ± 5 | 121 ± 16 |
| GH5 mannanase from *Trichoderma reesei* (mature polypeptide of SEQ ID NO: 11) | 45 ± 0.1 | 25 ± 1 | 41 ± 2 |

The given initial rates are an average of two replicates. ±one standard deviation is indicated.

The results in table 1 show that the GH26 mannanases of the invention degrade 3 different types of mannan: carob galactomannan, konjac glucomannan and guar gum galactomannan and have a significantly higher initial hydrolysis rate than the known GH5 mannanase from *Trichoderma reesei*.

Example 15: Conversion of Guar Gum Galactomannan

The conversion of guar gum galactomannan to mannanase using the GH26 mannanases of the invention was measured using different enzyme loads and compared to a GH5 beta-mannanase from *Trichoderma reesei* (mature polypeptide of SEQ ID NO: 11). The experiment was performed as described in example 14 and the results are presented in table 2 and FIG. 1.

TABLE 2

Percentage conversion of GH5 and GH26 mannanases on guar gum galactomannan

| Enzyme dilution factor | 1000/ (Enzyme dilution factor) | Conversion (%) | | |
|---|---|---|---|---|
| | | Mature polypeptide of SEQ ID NO: 2 | Mature polypeptide of SEQ ID NO: 5 | Mature polypeptide of SEQ ID NO: 11 |
| 3 | 333.3 | 33.8 | 32.5 | 7.7 |
| 9 | 111.1 | 28.8 | 27.9 | 7.7 |
| 27 | 37.0 | 16.0 | 17.3 | 6.5 |
| 81 | 12.3 | 6.7 | 7.5 | 2.9 |
| 243 | 4.1 | 2.0 | 2.4 | 0.8 |
| 729 | 1.4 | 0.6 | 0.7 | 0.1 |
| 2187 | 0.5 | 0.1 | 0.1 | 0.0 |

The results in table 2 and FIG. 1 show that the GH26 mannanases of the invention convert a significantly higher amount of guar gum galactomannan to mannan than the known GH5 mannanase from *Trichoderma reesei*.

Example 16: Deep-Cleaning Effects of GH26

A strain of *Brevundimonas* sp. isolated from laundry was used in the present example for demonstrating deep-cleaning effects, i.e. effects on disruption or removal of a biofilm. The strain was pre-grown on Tryptone Soya Agar (TSA) (pH 7.3) (CM0131; Oxoid Ltd, Basingstoke, UK) for 2-5 days at 30° C. From a single colony, a loop-full of was transferred to 10 mL of TSB and incubated for 16 hours at 30° C. with shaking (240 rpm). After propagation, cells were pelleted by centrifugation (Sigma Laboratory Centrifuge 6K15) (3000 g at 21° C. in 7 min) and resuspended in 10 mL of TSB diluted twice with milliQ water. Optical density (OD) at 600 nm was measured using a spectophometer (POLARstar Omega (BMG Labtech, Ortenberg, Germany). The *Brevundimonas* sp. cells were inoculated to $OD_{600\ nm}$ 0.03 in fresh TSB diluted twice with milliQ water, and 1.6 mL was added into each well of a 12-well polystyrene flat-bottom microplate (3512; Corning Incorporated, Corning, N.Y., USA), in which round swatches (diameter 2 cm) of sterile Polyester WFK30A was placed. After 24 h at 15° C. with shaking (100 rpm), growth medium was removed, and swatches were rinsed twice with 0.9% (w/v) NaCl.

Five rinsed swatches was mixed with five sterile Polyester WFK30A swatches in a 50 mL test tube and added 10 mL of wash liquor prepared by adding 3.33 g/l in water of a model detergent A containing 12% LAS, 11% AEO Biosoft N25-7 (NI), 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w) and 0.5 ppm of GH26 variants. Washes with model detergent A without added enzyme were made in parallel. Test tubes were placed in a Stuart rotator for 1 hour at 30° C. Wash liquor was removed, and swatches were rinsed twice with tap water and dried on filter paper over night.

Color difference (L values) was measured using a Color Eye (Macbeth Color Eye 7000 reflectance spectrophotometer). The measurements were made without UV in the incident light, and the L value from the CIE Lab color space was extracted. Data is represented as Delta L values meaning the L value of the swatch washed with GH26 variant minus the L value of swatch washed without enzyme. Deep cleaning effects were determined as Delta L higher than three. The GH26 mannanase from *Ascobolus stictoideus* (SEQ ID NO:

5) and from *Chaetomium virescens* (SEQ ID NO: 2) were compared with the commercial GH5 mannanase product Mannaway (obtainable from Novozymes A/S)

TABLE 3

Deep-cleaning effects of mannanases on *Brevundimonas* sp. swatches.

|  | L | ΔL (L$_{(enz)}$ − L$_{(no\ enz)}$) |
|---|---|---|
| No enzyme | 82.0 |  |
| Mannaway | 81.8 | −0.2 |
| GH26 mannanase from *Ascobolus stictoideus* (SEQ ID NO: 5) | 81.2 | −0.8 |
| GH26 mannanase from *Chaetomium virescens* (SEQ ID NO: 2) | 88.2 | 6.2 |

Example 17

Mass Spectrometry (MS/MS) sequencing confirmed that the tested samples contain the expected proteins: U19XX contains P335AV (SEQ ID NO: 5) and U19XY contains P335AW (SEQ ID NO: 2).

From a SDS-PAGE analysis it was observed that the P335AW protein exists in two versions with different molecular weight. For the molecules with the lowest molecular weight, the N-terminal was identified as TPS-VPRP (amino acid 121-127 in the sequence of P335AW (SEQ ID NO: 2). The N-terminal CBM35 of these molecules has been cleaved off but the core domain is intact. The molecules with a slightly higher molecular weight contain the intact N-terminal CBM35.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A method for degrading mannan, comprising applying a composition to the mannan, the composition including a polypeptide selected from the group consisting of:
   (a) a polypeptide having at least 90% sequence identity to SEQ ID NO: 3 or the mature polypeptide of SEQ ID NO: 2; and
   (b) a polypeptide having at least 90% sequence identity to SEQ ID NO: 6 or the mature polypeptide of SEQ ID NO: 5.

2. The method of claim 1, wherein the mannan is on the surface of a textile or hard surface.

3. The method of claim 1, wherein the mannan is used in fracturing of a subterranean formation perpetrated by a well bore.

4. The method of claim 3, wherein the mannan is a component in borehole filtercake.

5. A method for producing a coffee extract, comprising the steps:
   (a) providing roast and ground coffee beans;
   (b) adding to the coffee beans, water and a polypeptide;
   (c) incubating to make an aqueous coffee extract; and
   (d) separating the coffee extract from the extracted coffee beans;
   the polypeptide of step (b) selected from the group consisting of:
     (i) a polypeptide having at least 90% sequence identity to SEQ ID NO: 3 or the mature polypeptide of SEQ ID NO: 2; and
     (ii) a polypeptide having at least 90% sequence identity to SEQ ID NO: 6 or the mature polypeptide of SEQ ID NO: 5.

6. The method of claim 5, wherein step (b) further comprises adding an enzyme having β-1,3-galactanase activity.

7. A process for degrading a cellulosic material, comprising: treating the cellulosic material with an enzyme composition in the presence of a polypeptide selected from the group consisting of:
   (a) a polypeptide having at least 90% sequence identity to SEQ ID NO: 3 or the mature polypeptide of SEQ ID NO: 2; and
   (b) a polypeptide having at least 90% sequence identity to SEQ ID NO: 6 or the mature polypeptide of SEQ ID NO: 5.

8. A process for producing a fermentation product, comprising:
   (a) saccharifying a cellulosic material with an enzyme composition in the presence of a polypeptide;
   (b) fermenting the saccharified cellulosic material with one or more fermenting microorganisms to produce the fermentation product; and
   (c) recovering the fermentation product from the fermentation;
   the polypeptide of step (a) selected from the group consisting of:
     (i) a polypeptide having at least 90% sequence identity to SEQ ID NO: 3 or the mature polypeptide of SEQ ID NO: 2; and
     (ii) a polypeptide having at least 90% sequence identity to SEQ ID NO: 6 or the mature polypeptide of SEQ ID NO: 5.

9. The process of claim 8, wherein the cellulosic material is pretreated.

10. The process of claim 7, wherein the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

11. A process of fermenting a cellulosic material, comprising: fermenting the cellulosic material with one or more fermenting microorganisms, wherein the cellulosic material is saccharified with an enzyme composition in the presence of a polypeptide selected from the group consisting of:
   (a) a polypeptide having at least 90% sequence identity to SEQ ID NO: 3 or the mature polypeptide of SEQ ID NO: 2; and
   (b) a polypeptide having at least 90% sequence identity to SEQ ID NO: 6 or the mature polypeptide of SEQ ID NO: 5.

12. The process of claim 11, wherein the cellulosic material is pretreated before saccharification.

13. The process of claim 11, wherein the enzyme composition comprises one or more enzymes selected from the group consisting of cellulase, AA9 polypeptide, hemicellulase, esterase, expansin, ligninolytic enzyme, oxidoreductase, pectinase, protease, and swollenin.

14. A nucleic acid construct or expression vector, comprising a polynucleotide encoding a polypeptide operably linked to one or more control sequences that direct the production of the polypeptide in an expression host; the polypeptide selected from the group consisting of:
  (i) a polypeptide having at least 90% sequence identity to SEQ ID NO: 3 or the mature polypeptide of SEQ ID NO: 2; and
  (ii) a polypeptide having at least 90% sequence identity to SEQ ID NO: 6 or the mature polypeptide of SEQ ID NO: 5.

15. An isolated host cell, comprising a polynucleotide encoding a polypeptide operably linked to one or more control sequences that direct the production of the polypeptide; the polypeptide selected from the group consisting of:
  (i) a polypeptide having at least 90% sequence identity to SEQ ID NO: 3 or the mature polypeptide of SEQ ID NO: 2; and
  (ii) a polypeptide having at least 90% sequence identity to SEQ ID NO: 6 or the mature polypeptide of SEQ ID NO: 5.

16. A method of producing a polypeptide, comprising:
(a) cultivating the host cell of claim 15 under conditions conducive for production of the polypeptide; and
(b) recovering the polypeptide.

* * * * *